US010213192B2

(12) United States Patent
Capote

(10) Patent No.: US 10,213,192 B2
(45) Date of Patent: Feb. 26, 2019

(54) SURGICAL INSTRUMENT AND METHOD OF USE

(71) Applicant: Warsaw Orthopedic, Inc., Warsaw, IN (US)

(72) Inventor: Cristian A. Capote, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 24 days.

(21) Appl. No.: 14/800,337

(22) Filed: Jul. 15, 2015

(65) Prior Publication Data

US 2017/0014118 A1    Jan. 19, 2017

(51) Int. Cl.
*A61B 17/02*     (2006.01)
*A61B 90/57*     (2016.01)
*A61B 17/00*     (2006.01)

(52) U.S. Cl.
CPC ...... *A61B 17/0206* (2013.01); *A61B 17/0293* (2013.01); *A61B 90/57* (2016.02); *A61B 2017/0046* (2013.01); *A61B 2090/571* (2016.02)

(58) Field of Classification Search
CPC . A61B 17/02; A61B 17/0206; A61B 17/0218; A61B 17/0256; A61B 17/025; A61B 17/0293; A61B 2017/0212
See application file for complete search history.

(56) References Cited

U.S. PATENT DOCUMENTS

| 2,693,795 | A |   | 11/1954 | Greishaber |
|-----------|---|---|---------|------------|
| 3,626,471 | A |   | 12/1971 | Florin |
| 3,965,890 | A |   | 6/1976  | Gauthier |
| 5,027,793 | A |   | 7/1991  | Engelhardt et al. |
| 5,984,867 | A | * | 11/1999 | Deckman ........... A61B 17/0206 600/231 |
| 6,074,343 | A |   | 6/2000  | Nathanson et al. |
| 6,206,826 | B1 |  | 3/2001  | Matthews et al. |
| 6,254,532 | B1 | * | 7/2001 | Paolitto ............. A61B 17/0206 600/201 |
| 6,322,500 | B1 |  | 11/2001 | Sikra et al. |
| 6,416,469 | B1 |  | 7/2002  | Phung et al. |
| 6,599,240 | B2 |  | 7/2003  | Puchovsky et al. |
| 7,207,949 | B2 |  | 4/2007  | Miles et al. |
| 7,537,565 | B2 |  | 5/2009  | Bass |
| 7,582,058 | B1 |  | 9/2009  | Miles et al. |
| 7,691,057 | B2 |  | 4/2010  | Miles et al. |
| 7,785,253 | B1 | * | 8/2010 | Arambula ................ A61B 1/32 600/219 |

(Continued)

FOREIGN PATENT DOCUMENTS

WO    2015054070 A1    4/2015

*Primary Examiner* — Ellen C Hammond

(57) ABSTRACT

A surgical instrument includes an element connectable with a fixture. A first member is independently and selectively movable relative to the element and includes a part engageable with an incision in a cranial-caudal orientation relative to a body to space apart tissue. A second member is independently and selectively movable relative to the element and includes a part engageable with tissue of an anterior portion of the incision relative to the body. A third member is independently and selectively movable relative to the element and includes a part engageable with tissue of a posterior portion of the incision relative to the body. Systems and methods are disclosed.

20 Claims, 18 Drawing Sheets

(56) References Cited

U.S. PATENT DOCUMENTS

| | | | |
|---|---|---|---|
| 7,892,173 B2 | 2/2011 | Miles et al. | |
| 7,905,840 B2 | 3/2011 | Pimenta et al. | |
| 7,920,922 B2 | 4/2011 | Gharib et al. | |
| 7,935,051 B2 | 5/2011 | Miles et al. | |
| 7,962,191 B2 | 6/2011 | Marino et al. | |
| 8,000,782 B2 | 8/2011 | Gharib et al. | |
| 8,005,535 B2 | 8/2011 | Gharib et al. | |
| 8,016,767 B2 | 9/2011 | Miles et al. | |
| 8,038,611 B2 | 10/2011 | Raymond et al. | |
| 8,055,349 B2 | 11/2011 | Gharib et al. | |
| 8,062,218 B2 | 11/2011 | Sebastian et al. | |
| D652,519 S | 1/2012 | Miles et al. | |
| D652,921 S | 1/2012 | Miles et al. | |
| D652,922 S | 1/2012 | Miles et al. | |
| 8,114,019 B2 | 2/2012 | Miles et al. | |
| 8,133,173 B2 | 3/2012 | Miles et al. | |
| 8,137,284 B2 | 3/2012 | Miles et al. | |
| 8,165,653 B2 | 4/2012 | Marino et al. | |
| 8,172,750 B2 | 5/2012 | Miles et al. | |
| 8,182,423 B2 | 5/2012 | Miles et al. | |
| 8,187,179 B2 | 5/2012 | Miles et al. | |
| 8,192,356 B2 | 6/2012 | Miles et al. | |
| 8,192,357 B2 | 6/2012 | Miles et al. | |
| 8,231,528 B1 * | 7/2012 | Friedrich | A61B 17/02 600/201 |
| D666,292 S | 8/2012 | Miles et al. | |
| D666,294 S | 8/2012 | Miles et al. | |
| D666,923 S | 8/2012 | Miles et al. | |
| 8,244,343 B2 | 8/2012 | Gharib et al. | |
| 8,303,498 B2 | 11/2012 | Miles et al. | |
| 8,343,046 B2 | 1/2013 | Miles et al. | |
| 8,353,826 B2 | 1/2013 | Weiman | |
| 8,357,184 B2 | 1/2013 | Woolley et al. | |
| 8,535,320 B2 | 9/2013 | Woolley et al. | |
| 8,636,655 B1 | 1/2014 | Childs | |
| 8,882,662 B2 | 11/2014 | Charles | |
| 9,044,280 B1 | 6/2015 | Arambula et al. | |
| 2002/0002376 A1 * | 1/2002 | Gannoe | A61B 17/320016 606/167 |
| 2006/0224044 A1 | 10/2006 | Marchek et al. | |
| 2007/0208227 A1 | 9/2007 | Smith et al. | |
| 2011/0046448 A1 | 2/2011 | Paolitto et al. | |
| 2012/0245431 A1 | 9/2012 | Baudouin et al. | |
| 2012/0283521 A1 | 11/2012 | Smith et al. | |
| 2013/0190575 A1 | 7/2013 | Mast et al. | |
| 2013/0204091 A1 * | 8/2013 | Menendez | A61B 17/02 600/228 |
| 2014/0135584 A1 | 5/2014 | Lee et al. | |
| 2015/0018623 A1 * | 1/2015 | Friedrich | A61B 17/0206 600/206 |
| 2015/0018628 A1 * | 1/2015 | Friedrich | A61B 17/0206 600/214 |
| 2015/0088030 A1 | 3/2015 | Taylor | |
| 2015/0100129 A1 | 4/2015 | Waugh et al. | |
| 2015/0230787 A1 * | 8/2015 | Friedrich | A61B 17/0206 600/213 |
| 2015/0265265 A1 * | 9/2015 | Hynes | A61B 17/025 600/219 |
| 2015/0305731 A1 * | 10/2015 | Friedrich | A61B 90/30 600/216 |
| 2016/0192922 A1 * | 7/2016 | Friedrich | A61B 17/025 600/214 |
| 2017/0007227 A1 * | 1/2017 | Hynes | A61B 17/0206 |
| 2017/0014117 A1 * | 1/2017 | Capote | A61B 17/0206 |
| 2017/0014119 A1 * | 1/2017 | Capote | A61B 17/0206 |

* cited by examiner

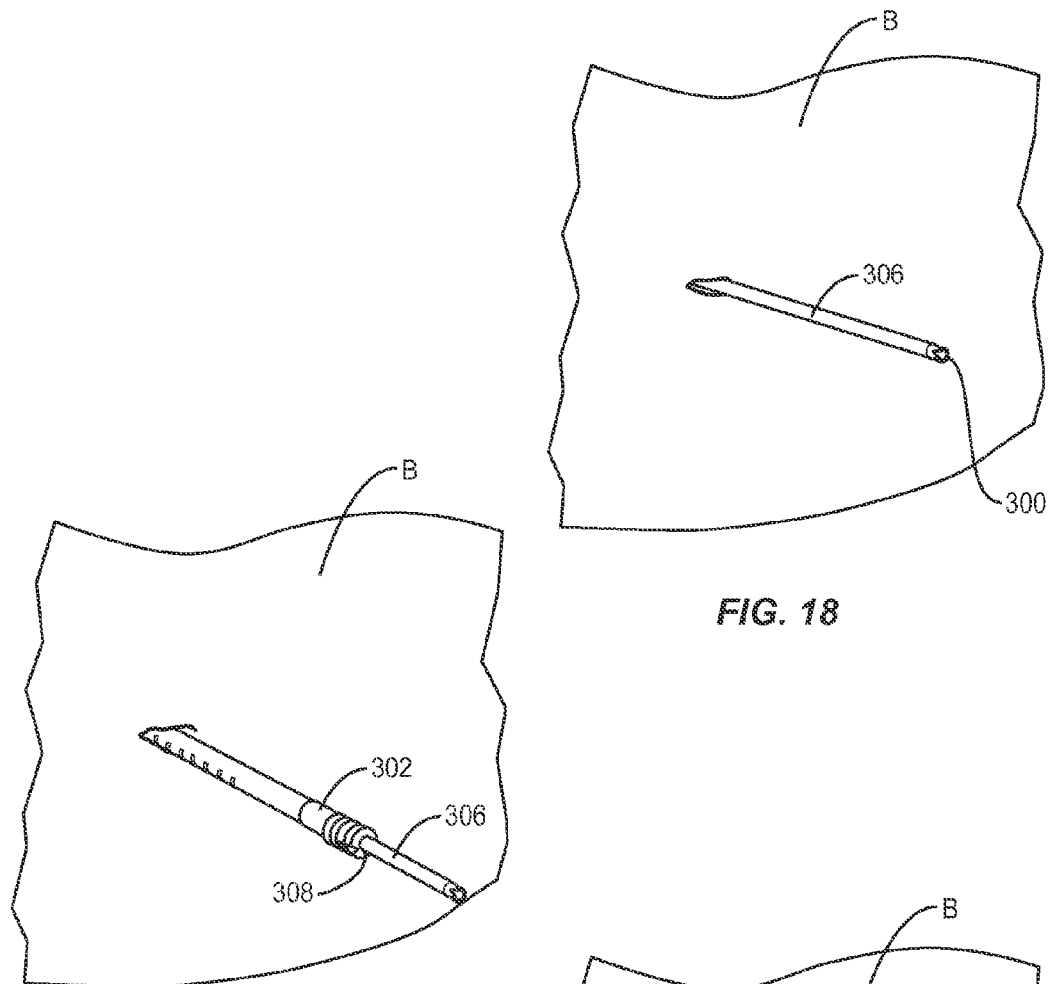
FIG. 18
FIG. 19
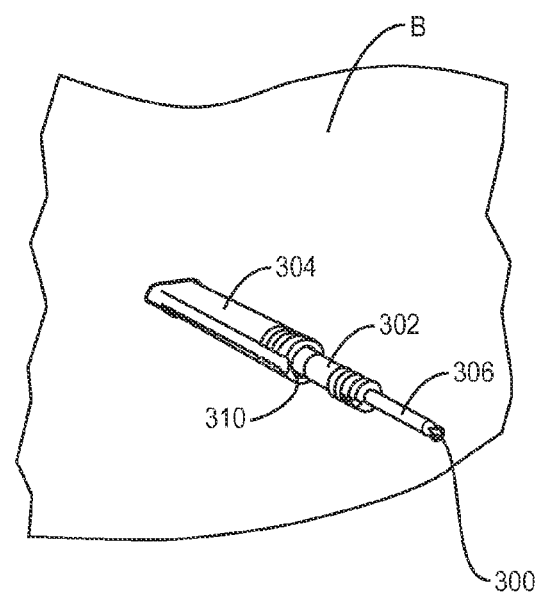
FIG. 20

SURGICAL INSTRUMENT AND METHOD OF USE

TECHNICAL FIELD

The present disclosure generally relates to medical devices for the treatment of musculoskeletal disorders, and more particularly to a surgical system and a method for treating a spine, which employ an oblique pathway.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy, corpectomy and implantable prosthetics. As part of these surgical treatments, spinal constructs, such as, for example, bone fasteners, spinal rods and interbody devices can be used to provide stability to a treated region. For example, during surgical treatment, surgical instruments can be used to deliver components of the spinal constructs to the surgical site for fixation with bone to immobilize a joint. This disclosure describes an improvement over these prior technologies.

SUMMARY

Systems and methods of use for accessing disc spaces via an oblique lateral approach are provided. In some embodiments, a surgical instrument is provided. The surgical instrument includes an element connectable with a fixture. A first member is independently and selectively movable relative to the element and includes a part engageable with an incision in a cranial-caudal orientation relative to a body to space apart tissue. A second member is independently and selectively movable relative to the element and includes a part engageable with tissue of an anterior portion of the incision. A third member is independently and selectively movable relative to the element and includes a part engageable with tissue of a posterior portion of the incision. The parts are disposable in a configuration to space tissue of the incision to define an oblique surgical pathway relative to a bilateral axis of the body.

BRIEF DESCRIPTION OF THE DRAWINGS

The present disclosure will become more readily apparent from the specific description accompanied by the following drawings, in which:

FIG. 18 is a perspective view of components of one embodiment of a system in accordance with the principles of the present disclosure disposed with a patient body;

FIG. 19 is a perspective view of components of one embodiment of a system in accordance with the principles of the present disclosure disposed with a patient body;

FIG. 20 is a perspective view of components of one embodiment of a system in accordance with the principles of the present disclosure disposed with a patient body;

DETAILED DESCRIPTION

Figure 1:
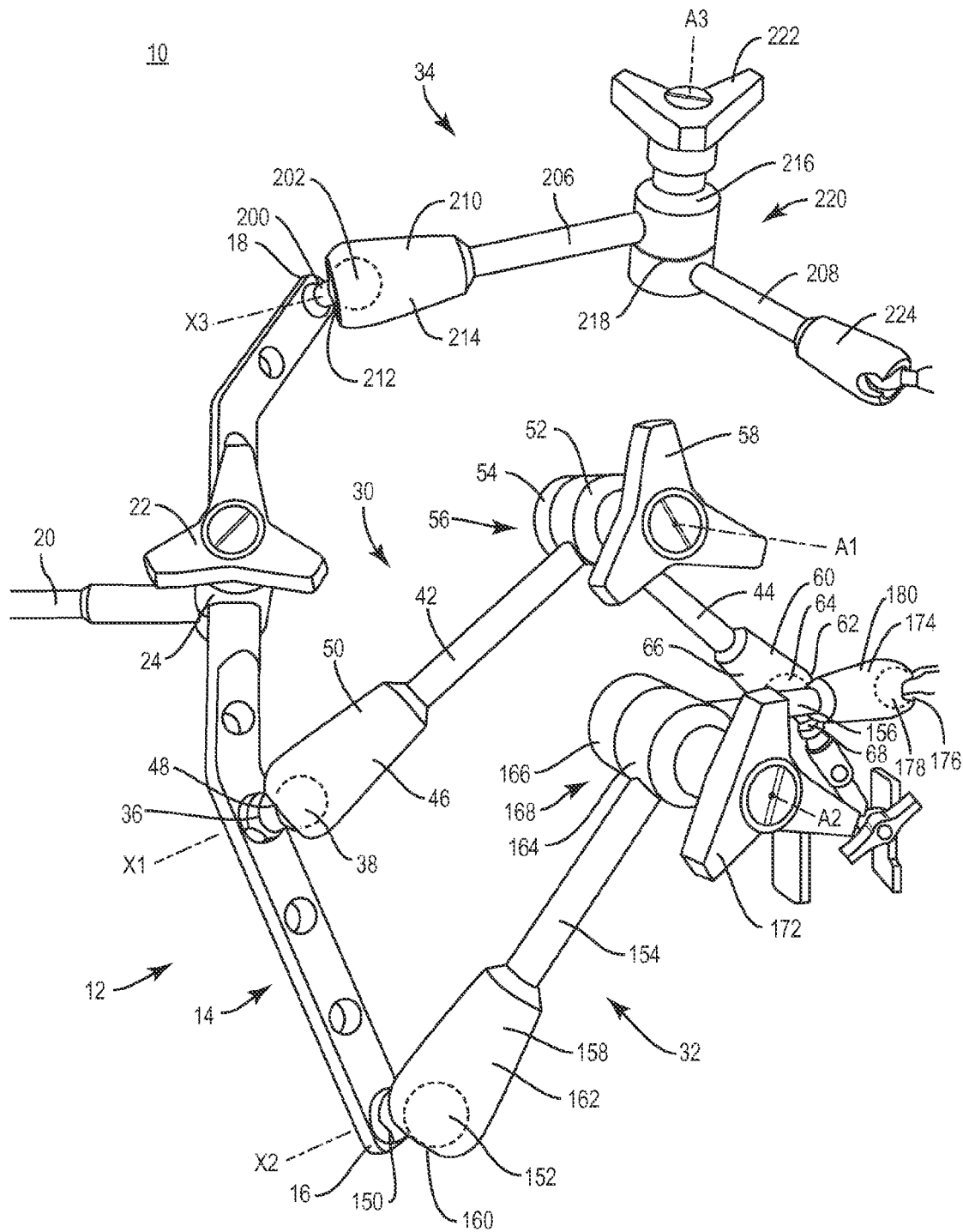
FIG. 1 is a perspective view of components of one embodiment of a surgical system in accordance with the principles of the present disclosure disposed with a patient body.
Figure 2:
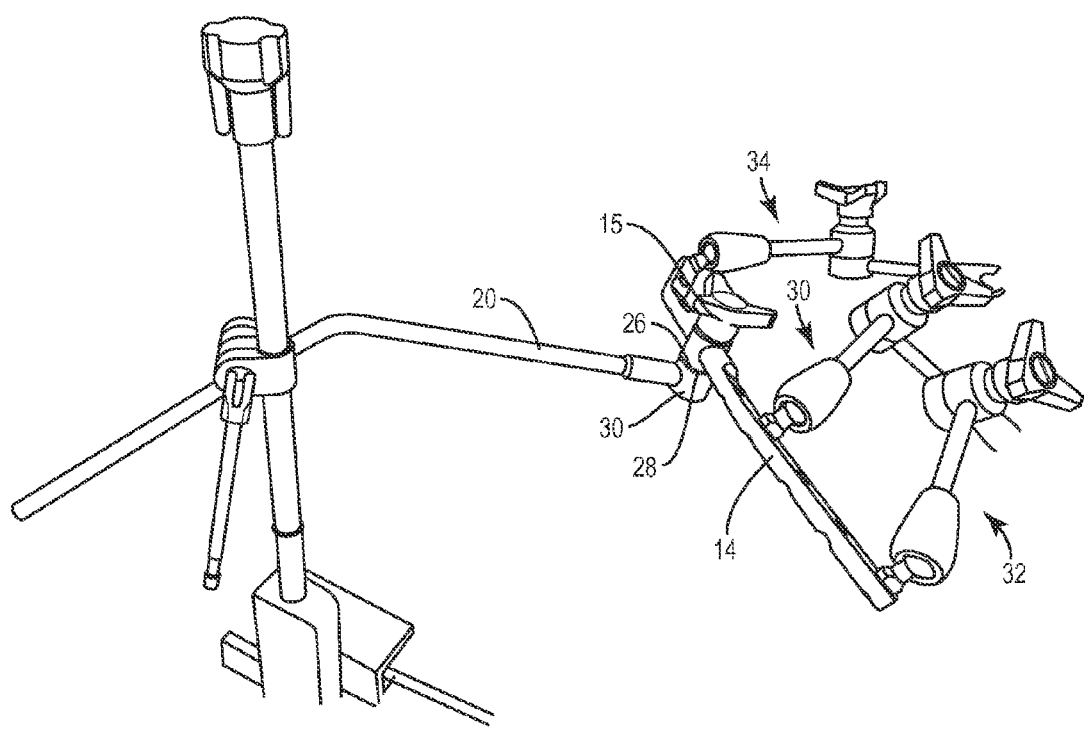
FIG. 2 is a perspective view of components of one embodiment of a surgical system in accordance with the principles of the present disclosure disposed with a patient body.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine, which employ an oblique surgical pathway, which may include an oblique-lateral surgical pathway. In one embodiment, the systems and methods of the present disclosure are employed with a spinal joint and fusion, for example, with a cervical, thoracic, lumbar and/or sacral region of a spine.

In some embodiments, the surgical system is employed with a method including an oblique lateral interbody fusion (OLIF) procedure in the lower lumbar region between an L1 vertebral body and an L5 vertebral body using an anterolateral operative corridor between a posterior psoas muscle and an anterior vasculature, such as, for example, the vena cava and aorta. In some embodiments, the patient is placed on their side, left side up, to position the vena cava on the right side of a centerline. In some embodiments, the surgical system displaces the psoas muscle posteriorly thereby avoiding teasing apart the muscle fibers and disrupting nerves located in the psoas muscle in the L1-L5 vertebral region. In some embodiments, the psoas muscle is numbed and/or paralyzed during the surgical procedure.

In some embodiments, the surgical system includes a surgical instrument, such as, for example, a retractor configured for use with an OLIF procedure for treating the L2-L5 vertebral region. In some embodiments, the surgical system includes non-modular components and/or attachments.

In some embodiments, the surgical system comprises a retractor configured for use with an OLIF procedure for treating the L2-L5 vertebral region for spinal access into an antero-lateral corridor of a body. In some embodiments, the surgical system comprises a triple arm retractor comprising three articulating arms attached to a fixed, straight rail. In some embodiments, the surgical system comprises a triple arm retractor comprising three articulating arms attached to a curved rail. In some embodiments, the surgical system comprises a triple arm retractor comprising three articulating arms attached to a bed clamp. In some embodiments, one of the arms of the retractor holds a two-blade retractor rack. In some embodiments, the surgical system comprises a universal connector configured to attach various blades and racks to the arms of a frame.

In some embodiments, the surgical system comprises a triple arm frame retractor system. In some embodiments, the triple arm frame retractor system comprises three largely independent arms used in combination with a 2 blade rack to position three or more blades of a retractor configured for use with an OLIF procedure for treating the L2-L5 vertebral region. In some embodiments, the surgical system comprises a retractor configured for use with an OLIF procedure for treating the L2-L5 vertebral region that utilizes an oblique approach to the L2-L5 intervertebral disc spaces with the patient positioned in the lateral decubitus position. In some embodiments, the retractor comprises three flex arms comprising one or many articulation points attached along a straight or curved rail. In some embodiments, the straight or curved rail is configured to attach directly to a surgical table. In some embodiments, the three flex arms comprising one or many articulation points configured to attach to a bed clamp hub configured to attach directly to the surgical table.

In some embodiments, the surgical system is employed with a method for treating a spinal cord. In some embodiments, the method includes the step of localizing and dilating a surgical site using a solid first dilator. In some embodiments, the method includes the step of positioning a first solid/non-cannulated dilator at the surgical site anteriorly and facilitates localization of the disc space. In some embodiments, the method includes the step of positioning remaining dilators at the surgical site. In some embodiments, the method includes the step of positioning a retractor.

In some embodiments, the surgical system comprises pins disposed through blades of the retractor. In some embodiments, the surgical system comprises a rack retractor having a first round blade and a second round blade configured for translation and blade rotation in a cranial-caudal direction. In some embodiments, the retractor is connected to a first flex arm and is open. In some embodiments, a first, a second and a third flex arm are mounted to a common bar. In some embodiments, the first flex arm secures a rack and two blades. In some embodiments, the second flex arm attaches to a third blade and the retractor blades are opened. In some embodiments, the second flex arm secures the third blade and is positioned using a handle. In some embodiments, the third blade retracts in an anterior direction. In some embodiments, the third flex arm attaches to a fourth blade. The third flex arm secures the fourth blade and is positioned using the handle. In some embodiments, the fourth blade retracts in a posterior direction. In some embodiments, the common bar is secured using a bedrail and a second bar. In some embodiments, three flex arms are mounted to the common bar. In some embodiments, the common bar is secured to a bedrail using the second bar. In some embodiments, both the common bar and the bedrail can articulate.

In some embodiments, the retractor comprises a third blade attachment. In some embodiments, the method comprises the step of positioning a two bladed rack retractor, as described herein. In some embodiments, a third blade is attached to the retractor using a smaller flex arm that directly attaches to a single table mounted flex arm and the third blade retracts anteriorly. In some embodiments, the surgical system comprises a single flex arm and a bedrail attachment. In some embodiments, a third blade is added to the retractor without the use of a common bar. In some embodiments, a single flex arm is used to secure the retractor to the bedrail.

In some embodiments, the surgical system comprises a rack retractor. In some embodiments, the rack retractor allows translation and rotation of blades. In some embodiments, the surgical system comprises a fixation member and a rack connection. In some embodiments, a connector for retractor blades is provided that offers multiple degrees of freedom. In some embodiments, the connector is used to connect a rack to a common rail.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-5, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 includes a surgical instrument, such as, for example, a surgical retractor 12, as shown in FIG. 1. Surgical retractor 12 includes an element, such as, for example, a rail 14. Rail 14 is configured for connection with a fixture, such as, for example, an arm 20 of stationary surgical equipment, such as, for example, a surgical table (not shown). Rail 14 is configured to facilitate placement and/or orientation of retractor 12 relative to subject body B and/or an incision in connection with a surgical procedure.

Rail 14 extends between an end 16 and an end 18. Rail 14 extends with angled sections between ends 16, 18. In some embodiments, rail 14 is movable relative to arm 20 and is lockable with arm 20 in a selected position and/or orientation. In some embodiments, rail 14 includes a knob 22 that locks rail 14 with arm 20 in a selected position and/or orientation relative to the surgical table and/or a patient body, as described herein. In some embodiments, knob 22 is connected with a collar 24 having a radially splined surface 26 that engages a radially splined surface 28 of a collar 30 of arm 20 to facilitate incremental and selective positioning of rail 14 relative to the surgical table. Upon selective positioning and orientation of rail 14 relative to arm 20, knob 22 is rotated to force the splined surfaces into engagement for locking rail 14 in position with arm 20.

In some embodiments, rail 14 can include a single or multiple rails, each being spaced apart from one another and disposed in various orientations, such as, for example, offset, staggered, transverse, perpendicular and/or parallel. In some embodiments, all or only a portion of rail 14 may be variously configured and dimensioned, such as, for example, planar, concave, convex, polygonal, irregular, uniform, non-uniform, staggered, tapered, consistent or variable.

Surgical retractor 12 includes a plurality of members, such as, for example, a plurality of retractor arms 30, 32 and 34, as described herein. Retractor arms 30, 32 and 34 are attached with rail 14 such that one or a plurality of arms 30, 32 and 34 are movable in one or a plurality of degrees of freedom to one or a plurality of orientations relative to rail 14, stationary surgical equipment and/or subject body B in connection with a surgical procedure. In some embodiments, the degrees of freedom of movement of one or more of arms 30, 32 and 34 to one or a plurality of orientations relative to rail 14, stationary surgical equipment and/or subject body B can include one or a plurality of degrees of movement in translation, one or a plurality of degrees of movement in rotation, planar movement such as a four bar linkage, spherical movement such as poly-axial and/or joints or links such as a kinematic chain. In some embodiments, the degrees of movement in translation can include up, down, left, right, forward and/or backward. In some embodiments, the degrees of movement in rotation can include tilting, swiveling and/or pivoting in one or a plurality directions.

In some embodiments, arms 30, 32 and 34 are independently and selectively movable relative to rail 14, stationary surgical equipment and/or subject body B. In some embodiments, arms 30, 32 and 34 comprise a plurality of independent fixation arms that each articulate with several degrees of freedom relative to rail 14, stationary surgical equipment and/or subject body B. In some embodiments, the configuration of surgical retractor 12 provides arms 30, 32 and 34 that can be employed with a variety of surgical applications, as described herein. In some embodiments, the configuration of surgical retractor 12 provides arms 30, 32 and 34 connected to parts, such as, for example, blades that can be disposed at a selected angle of trajectory and unconstrained by placement of adjacent blades. In some embodiments, arms 30, 32 and 34 are attached with rail 14 in a modular configuration to facilitate attachment at multiple attachment points, as described herein.

Figure 4:
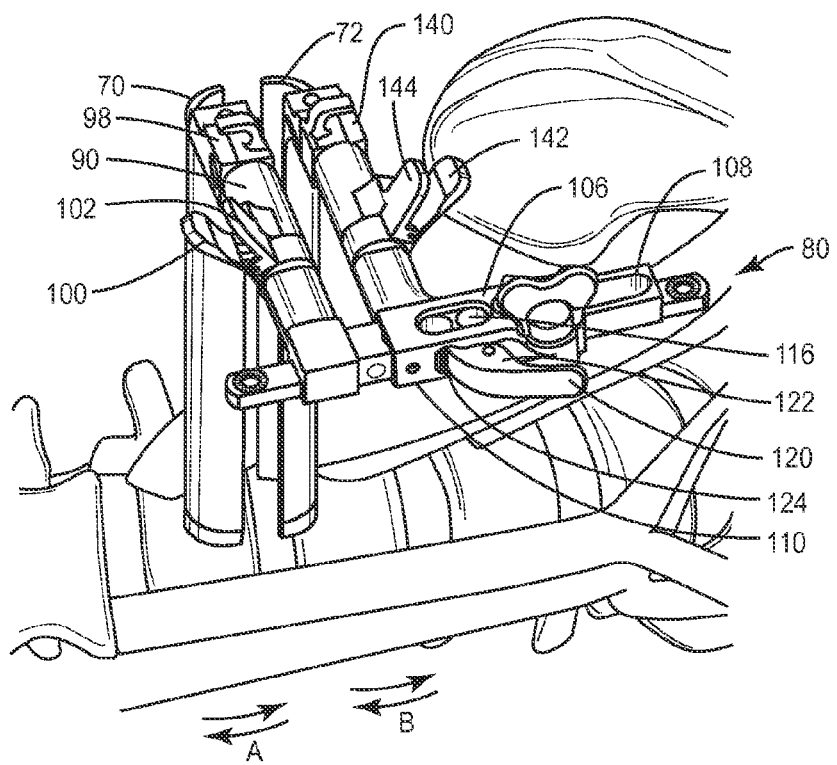
FIG. 4 is a perspective view of components of one embodiment of a system in accordance with the principles of the present disclosure disposed with a patient body.

Arm 30 is connected with rail 14 at a projection 36 adjacent an intermediate portion of rail 14. Projection 36 defines an axis X1. Projection 36 includes a bearing, such as, for example, a ball 38 that is connected with arm 30, as described herein. Arm 30 is movable in a plurality of degrees of freedom to one or a plurality of orientations, relative to rail 14, stationary surgical equipment and/or subject body B in connection with a surgical procedure. In some embodiments, arm 30 is independently and selectively moveable relative to rail 14 about axis X1 to facilitate positioning of a part, such as, for example, a blades 70, 72, as shown in FIG. 4 and described herein.

Arm 30 includes an extension 42 and an extension 44. Extension 42 includes a tubular collar 46 that defines a socket 48 configured for disposal of ball 38. Ball 38 and collar 46 form a spheroidal joint, such as, for example, a ball joint 50 that facilitates relative movement of extension 42 and rail 14. Ball 26 is fixed with rail 14 and collar 32 is movable thereabout such that extension 42 is movable in a plurality of degrees of freedom to one or a plurality of orientations, such as, for example, poly-axial relative to rail 14, stationary surgical equipment and/or subject body B in connection with a surgical procedure. In some embodiments, ball joint 50 provides rotation of extension 42 relative to projection 36 and disposal of extension 42 at a plurality of orientations relative to axis X1. In some embodiments, extension 42 is movable relative to rail 14 between a first orientation and a second orientation in which extension 42 is moveable through an angular range relative to axis X1. In some embodiments, the orientations relative to axis X1 may include, such as, for example, transverse, perpendicular, angular orientations such as acute or obtuse, coaxial and/or may be offset or staggered.

Extension 42 includes a disc shaped collar 52 that is connected to a disc shaped collar 54 of extension 44, as described herein. Collars 52, 54 form a pivot joint 56 that is disposable between a movable orientation and a locked orientation. Pivot joint 56 defines an axis A1 disposed transverse to axis X1. Collars 52, 54 are relatively rotatable about axis A1 to facilitate rotation of extension 44 relative to extension 42 for positioning of blades 70, 72 relative to rail 14, stationary surgical equipment and/or subject body B.

Pivot joint 56 includes a knob 58 that locks collar 52 with collar 54 such that extensions 42, 44 are disposed in a selected relative position and/or orientation relative to rail 14, stationary surgical equipment and/or subject body B. In some embodiments, knob 58 is connected with collar 52 having a radially splined surface that engages a radially splined surface of collar 54 to facilitate incremental and selective positioning of extensions 42, 44. Upon selective positioning and orientation of extensions 42, 44, knob 58 is rotated to force the splined surfaces into engagement for locking extension 42 in position with extension 44.

Extension 44 includes a tubular collar 60 that defines a socket 62. Socket 62 is configured for disposal of a bearing, such as, for example, a ball 64. Ball 64 and collar 60 form a spheroidal joint, such as, for example, a ball joint 66 that facilitates relative movement of blades 70, 72 and extension 44. Blades 70, 72 are movable in a plurality of degrees of freedom to one or a plurality of orientations, relative to extension 44, stationary surgical equipment and/or subject body B in connection with a surgical procedure. In some embodiments, blades 70, 72 is independently and selectively moveable relative to extension 44 about axis X1 to facilitate positioning of blades 70, 72, as described herein.

Extension 44 includes a projection 68 that includes ball 64 for engagement with socket 62, as described herein, to facilitate relative movement of blades 70, 72 and extension 44 in a plurality of degrees of freedom, such as poly-axial to one or a plurality of orientations. Projection 68 is configured for engagement with blades 70, 72 for positioning blades 70, 72 for engagement with an incision in a cranial-caudal orientation relative to a body to space apart tissue, as described herein. Blades 70, 72 are disposable in a configuration to space tissue of the incision to define an oblique surgical pathway P relative to a bilateral axis of the body, as described herein. Blades 70, 72 are configured to achieve a unique angle of trajectory and are unconstrained by placement of adjacent blades, as described herein.

Figure 5:
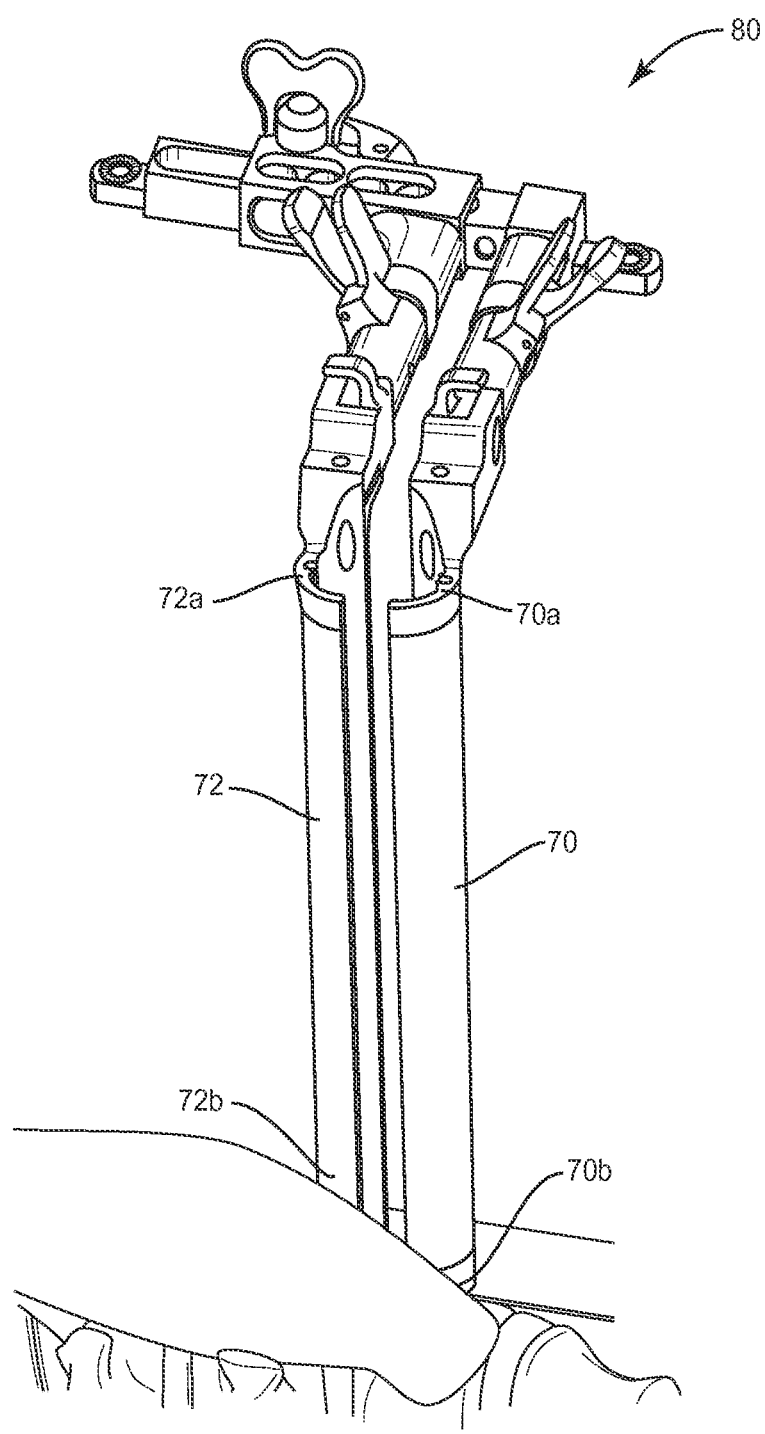
FIG. 5 is a perspective view of components of one embodiment of a surgical system in accordance with the principles of the present disclosure disposed with a patient body.
Figure 6:
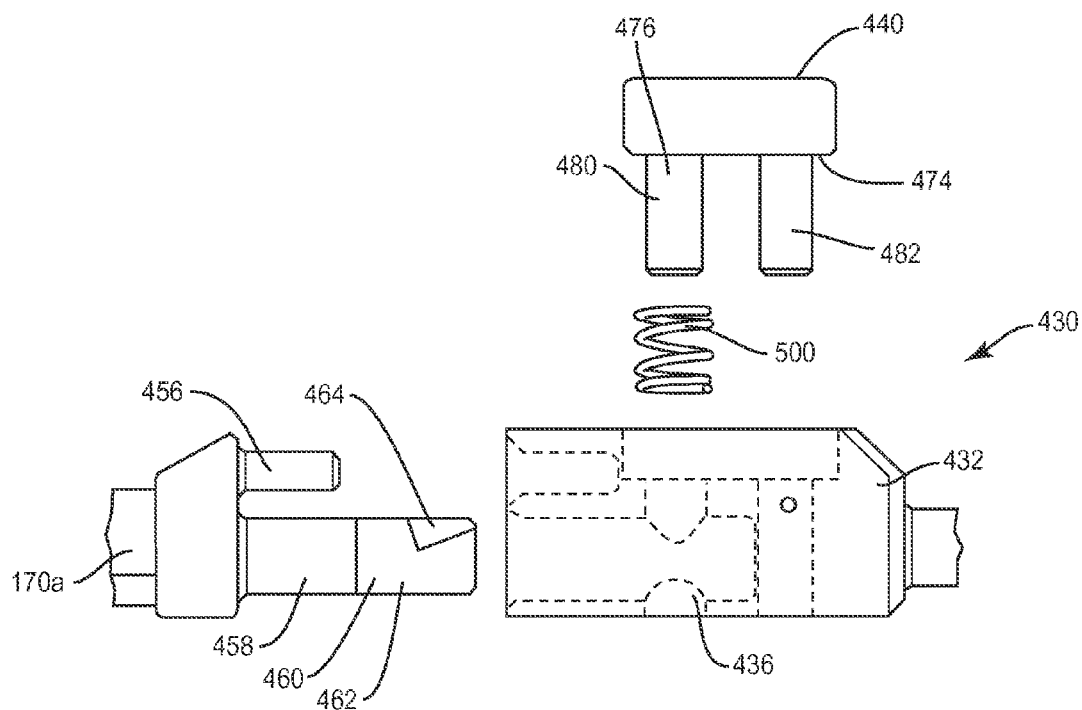
FIG. 6 is a break away side view of components of one embodiment of a surgical system in accordance with the principles of the present disclosure with parts separated.
Figure 29:
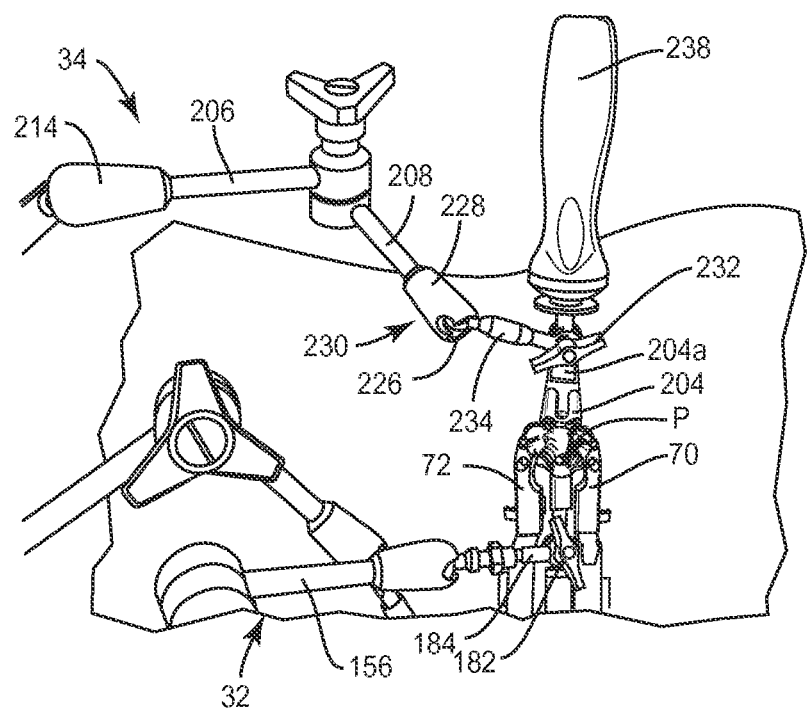
FIG. 29 is a side view of components of one embodiment of a system in accordance with the principles of the present disclosure disposed with a patient body.

Blade 70 extends between an end 70a and an end 70b, which may comprise a blade tip, as shown in FIG. 5. Blade 70 includes an outer surface configured for engaging and spacing apart tissue. Blade 70 includes an inner surface configured to define a portion of surgical pathway P (FIG. 29). Blade 72 extends between an end 72a and an end 72b, which may comprise a blade tip. Blade 72 includes an outer surface configured for engaging and spacing apart tissue. Blade 72 includes an inner surface configured to define a portion of surgical pathway P. Blades 70, 72 include a cylindrical configuration to facilitate insertion and movement of surrounding tissue and muscle. In some embodiments, all or only a portion of blade 70 and/or blade 72 may have various cross-section configurations, such as, for example, arcuate, oblong, rectangular, polygonal, undulating, irregular, uniform, non-uniform, consistent, variable, and/or U-shape.

Figure 21:
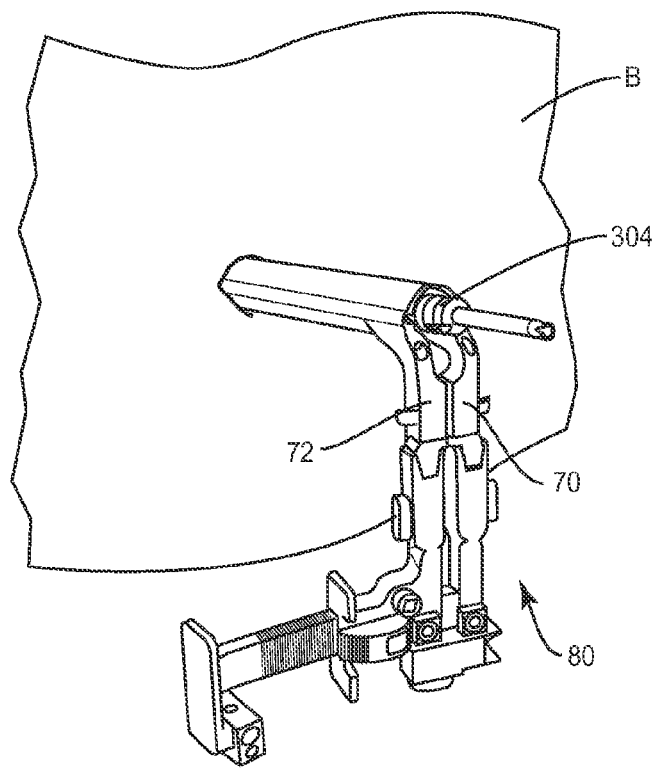
FIG. 21 is a perspective view of components of one embodiment of a system in accordance with the principles of the present disclosure disposed with a patient body.
Figure 25:
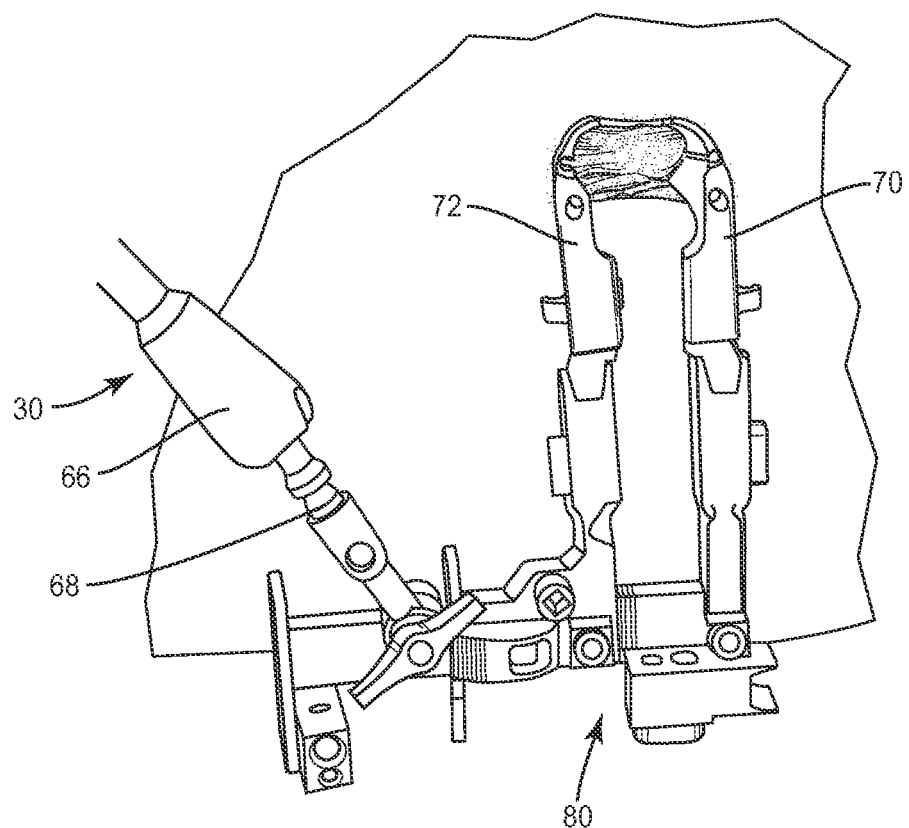
FIG. 25 is a perspective view of components of one embodiment of a system in accordance with the principles of the present disclosure disposed with a patient body.
Figure 26:
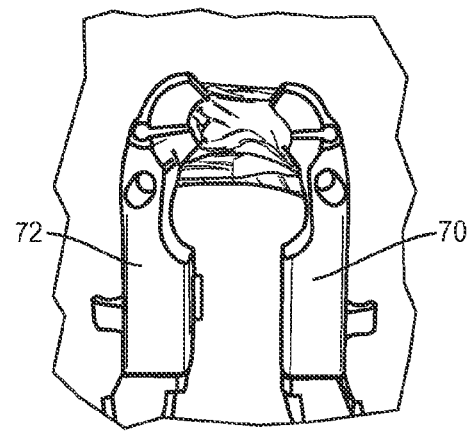
FIG. 26 is a perspective view of components of one embodiment of a system in accordance with the principles of the present disclosure disposed with a patient body.

Blades 70, 72 are movable relative to each other between a closed configuration, as shown for example in FIG. 21, and an open configuration, as shown for example in FIG. 25, such that blades 70, 72 are spaced apart to define a portion of surgical pathway P and facilitate spacing of tissue, as described herein. In some embodiments, blades 70, 72 may be disposed in one or a plurality of open configurations of varying degrees of spacing of blades 70, 72, and/or configurations between open and closed configurations.

Figure 3:
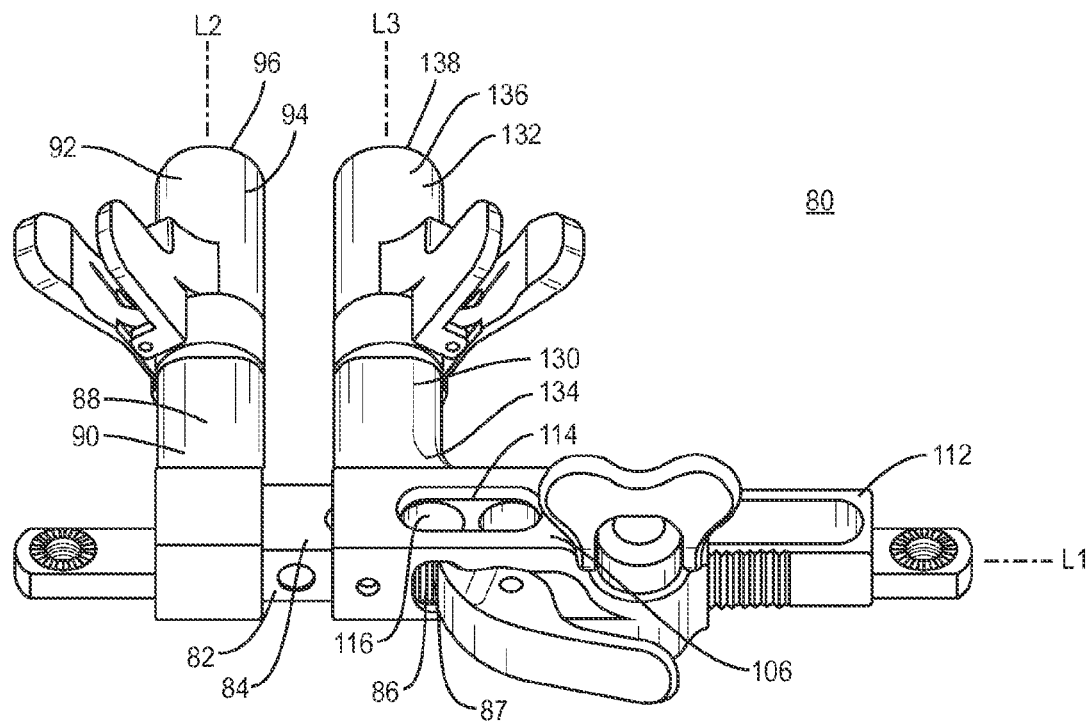
FIG. 3 is a perspective view of components of one embodiment of a surgical system in accordance with the principles of the present disclosure.

Blades 70, 72 are configured for connection with a rack retractor assembly 80, as shown in FIGS. 3-5. Rack retractor assembly 80 is configured to dispose blades 70, 72 with an incision in a cranial-caudal orientation to rotate and/or translate blades 70, 72 relative to arm 30 to space tissue, as described herein. Rack retractor assembly 80 includes a member, such as, for example, a shaft 82. Shaft 82 defines a longitudinal axis L1 and an outer surface 84. Outer surface 84 includes a rack 86. Rack 86 includes a plurality of teeth 87 configured to engage a member, as described herein, for selective positioning of blades 70, 72 to provide a range of spacing and/or distraction of blades 70, 72 for selective spacing of tissue at a surgical site. In some embodiments, shaft 82 may include a grip surface. The grip surface may include a surface that is configured for engagement with the hand of a practitioner, such as, for example, a finger, which can include a thumb. In some embodiments, the grip surface may include alternative surface configurations, which can be, for example, smooth, rough, mesh, porous, semi-porous, dimpled, arcuate, undulating, pointed and/or textured.

Shaft 82 includes an arm 88 extending therefrom along an axis L2 transverse to axis L1. Arm 88 extends in a perpendicular orientation from shaft 82 along the same plane. In some embodiments, arm 88 may be oriented along axis L2 in alternate configurations, such as, for example, parallel, co-axial, angularly offset, offset and/or staggered relative to axis L1. Arm 88 extends from an end 90 to an end 92. End 90 includes an interface configuration that mates with one of blades 70, 72, as described herein.

End 92 includes a mating shaft 94 that is cylindrical and includes an inner surface 96. In some embodiments, inner surface 96 comprises splines disposed in an axial orientation along axis L2. The spline configuration provides a mounting and alignment configuration for providing a snap fit between blade 70 and arm 88. In some embodiments, mating shaft 94 may have alternate cross section configurations, such as, for example, oval, oblong, triangular, rectangular, square, polygonal, irregular, uniform, non-uniform, variable and/or tapered. In some embodiments, all or only a portion of surface 96 may have alternate surface configurations, such as, for example, rough, threaded for connection with other instruments, arcuate, undulating, porous, semi-porous, dimpled, polished and/or textured.

Blade 70 comprises an arm 98 and is configured for engagement with shaft 94. Arm 98 provides a mounting and alignment configuration for mating blade 70 with arm 88. In some embodiments, arm 98 includes a surface that defines a spline configuration (not shown). The spline configuration provides a mounting and alignment configuration with shaft 94.

Shaft 94 includes a flange 100 engageable with a lever 102 to facilitate rotation of arm 88. Lever 102 has a flip-up configuration and facilitates rotation of arm 88 upon fixation of blade 70 with arm 88, as described herein. Lever 102 can be manipulated to rotate arm 88 in the opposing directions, as shown by arrows A in FIG. 4.

A housing 106 extends along axis L1 between an end 108 and an end 110. Housing 106 includes an outer surface 112 and an inner surface 114. Inner surface 114 defines an interior cavity 116 configured for translation along shaft 82 to translate blade 72, as described herein. In some embodiments, all or only a portion of housing 106 may have alternate cross section configurations, such as, for example, oblong, triangular, square, polygonal, irregular, uniform, non-uniform, offset, staggered, undulating, arcuate, variable and/or tapered.

Housing 106 includes a lock, such as, for example, a latch 120 that is releasably engageable with shaft 82 to selectively distract and/or space apart blades 70, 72 in a fixed orientation. Latch 120 includes a lever 122 that extends between a first end and a second end. The first end of lever 122 includes a knurled surface to facilitate engagement and/or gripping by a practitioner. The second end of lever 122 includes a protrusion 124 configured to engage teeth 87 to fix shaft 82 relative to housing 106. Lever 122 is mounted to housing 106 via a fulcrum and is configured for pivotal movement relative to housing 106 and shaft 82.

Lever 122 is engageable for pivotable movement between a non-locking configuration such that the protrusion is released from engagement with teeth 87 and shaft 82 is freely slidable relative to housing 106 to selectively position the blades 70, 72, and a locking configuration such that lever 122 is released from manipulative engagement such that the protrusion engages teeth 87 and shaft 82 is fixed relative to housing 106. In the locking configuration of lever 122, blades 70, 72 are selectively distracted to space apart tissue. In some embodiments, latch 120 includes a spring (not shown) that resiliently biases lever 122 to the locked configuration.

Rack retractor assembly 80 includes an arm 130 extending along an axis L3 transverse to axis L1. Arm 130 extends in a perpendicular orientation from housing 106 along the same plane. In some embodiments, arm 130 may be oriented along axis L3 in alternate configurations, such as, for example, parallel, co-axial, angularly offset, offset and/or staggered relative to axis L1. Arm 130 extends from an end 132 to an end 134. End 132 includes a blade interface configuration that mates with blade 72.

End 132 includes a mating shaft 136 that is cylindrical and includes an inner surface 138. In some embodiments, inner surface 138 comprises splines disposed in an axial orientation along axis L3. The spline configuration provides a mounting and alignment configuration for providing a snap fit between blade 72 and arm 130. In some embodiments, mating shaft 136 may have alternate cross section configurations, such as, for example, oval, oblong, triangular, rectangular, square, polygonal, irregular, uniform, non-uniform, variable and/or tapered. In some embodiments, all or only a portion of shaft 136 may have alternate surface configurations, such as, for example, rough, threaded for connection with other instruments, arcuate, undulating, porous, semi-porous, dimpled, polished and/or textured.

Blade 72 includes an arm 140 configured for engagement with shaft 136. Arm 140 provides a mounting and alignment configuration for mating blade 72 with arm 130. In some embodiments, arm 140 includes a surface that defines a spline configuration (not shown). The spline configuration provides a mounting and alignment configuration with shaft 136.

Shaft 136 includes a flange 142 engageable to facilitate rotation of a lever 144 and arm 140. Lever 144 has a flip-up configuration and facilitates rotation of arm 130 upon fixation of blade 72 with arm 130, as described. Lever 144 can be manipulated to rotate arm 130, in the direction shown by arrows B in FIG. 4.

Figure 27:
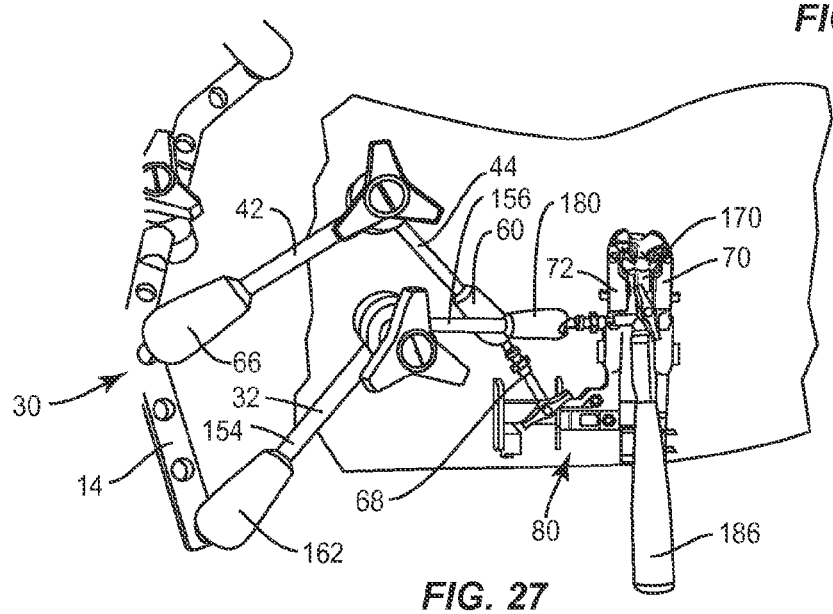
FIG. 27 is a side view of components of one embodiment of a system in accordance with the principles of the present disclosure disposed with a patient body.

Arm 32 is connected with rail 14 at a projection 150 adjacent an end portion of rail 14, as shown in FIG. 1. Projection 150 defines an axis X2. Projection 150 includes a bearing, such as, for example, a ball 152 that is connected with arm 32, as described herein. Arm 32 is movable in a plurality of degrees of freedom to one or a plurality of orientations, relative to rail 14, stationary surgical equipment and/or subject body B in connection with a surgical procedure. In some embodiments, arm 32 is independently and selectively moveable relative to rail 14 about axis X2 to facilitate positioning of a part, such as, for example, a blade 170 (FIG. 27), as described herein.

Arm 32 includes an extension 154 and an extension 156. Extension 154 includes a tubular collar 158 that defines a socket 160 configured for disposal of ball 152. Ball 152 and collar 158 form a spheroidal joint, such as, for example, a ball joint 162 that facilitates relative movement of extension 154 and rail 14. Ball 152 is fixed with rail 14 and collar 158 is movable thereabout such that extension 154 is movable in a plurality of degrees of freedom to one or a plurality of orientations, such as, for example, poly-axial relative to rail 14, stationary surgical equipment and/or subject body B in connection with a surgical procedure. In some embodiments, ball joint 162 provides rotation of extension 154 relative to projection 150 and disposal of extension 154 at a plurality of orientations relative to axis X2. In some embodiments, extension 154 is movable relative to rail 14 between a first orientation and a second orientation in which extension 154 is moveable through an angular range relative to axis X2. In some embodiments, the orientations relative to axis X2 may include, such as, for example, transverse, perpendicular, angular orientations such as acute or obtuse, coaxial and/or may be offset or staggered.

Extension 154 includes a disc shaped collar 164 that is connected to a disc shaped collar 166 of extension 156, as described herein. Collars 164,166 form a pivot joint 168 that is disposable between a movable orientation and a locked orientation. Pivot joint 168 defines an axis A2 disposed transverse to axis X2. Collars 164,166 are relatively rotatable about axis A2 to facilitate rotation of extension 156 relative to extension 154 for positioning of blade 170 relative to rail 14, stationary surgical equipment and/or subject body B.

Pivot joint 168 includes a knob 172 that locks collar 164 with collar 166 such that extensions 154,156 are disposed in a selected relative position and/or orientation relative to rail 14, stationary surgical equipment and/or subject body B. In some embodiments, knob 172 is connected with collar 164 having a radially splined surface that engages a radially splined surface of collar 166 to facilitate incremental and selective positioning of extensions 154, 156. Upon selective positioning and orientation of extensions 154, 156, knob 172 is rotated to force the splined surfaces into engagement for locking extension 154 in position with extension 156.

Extension 156 includes a tubular collar 174 that defines a socket 176. Socket 176 is configured for disposal of a bearing, such as, for example, a ball 178. Ball 178 and collar 174 form a spheroidal joint, such as, for example, a ball joint 180 that facilitates relative movement of blade 170 and extension 156. Blade 170 is movable in a plurality of degrees of freedom to one or a plurality of orientations, relative to extension 156, stationary surgical equipment and/or subject body B in connection with a surgical procedure. In some embodiments, blade 170 is independently and selectively moveable relative to extension 156 about axis X2 to facilitate positioning of blade 170, as described herein.

Extension 156 includes a clamp 182 (FIG. 29) for connection with blade 170. Clamp 182 is adjustable for releasable engagement with blade 170 to fix blade 170 in a selected orientation with arm 32. Clamp 182 includes a projection 184 that includes ball 178 for engagement with socket 176 as described herein, to facilitate relative movement of blade 170 and extension 156 in a plurality of degrees of freedom, such as poly-axial to one or a plurality of orientations. In some embodiments, clamp 182 includes a surface that defines a cavity (not shown) configured for disposal of an arm 170a (FIG. 28) of blade 170, as described herein. In some embodiments, clamp 182 includes a jaw (not shown) configured for translation within the cavity by actuation of a handle 186. Handle 186 is rotated such that the jaw engages arm 170a to fix blade 170 with clamp 182. In some embodiments, blade 170 in connected with a handle 186 configured to facilitate manipulation of blade 170.

In some embodiments, blade 170 is configured for disposal in an anterior orientation and engageable with tissue of a substantially anterior portion of an incision relative to subject body B, as described herein. In some embodiments, blade 170 is disposable in a configuration to space tissue of the incision to define an oblique surgical pathway P relative to a bilateral axis of subject body B, as described herein. In some embodiments, blade 170 is movable relative to extension 156 between a first orientation and a second orientation in which blade 170 is moveable through an angular range relative to extension 170. In some embodiments, blade 170 is configured to achieve a unique angle of trajectory and is unconstrained by placement of adjacent blades, as described herein. In one embodiment, blade 170 extends between a first end and a second end.

Figure 30:
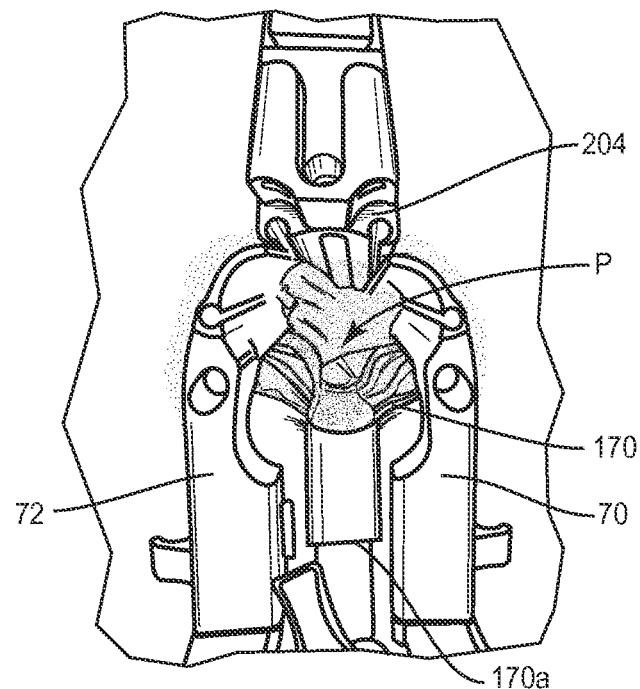
FIG. 30 is a plan view of components of one embodiment of a system in accordance with the principles of the present disclosure disposed with a patient body.

In some embodiments, blade 170 includes an outer surface configured for engaging and spacing apart tissue. Blade 170 includes an inner surface configured to define a portion of surgical pathway P. Blade 170 includes arm 170a, as shown in FIG. 30, configured for engagement with arm 60 and or an adaptor, as described herein.

Arm 34 is connected with rail 14 at a projection 200 adjacent an end portion of rail 14. Projection 200 defines an axis X3. Projection 200 includes a bearing, such as, for example, a ball 202 that is connected with arm 34, as described herein. Arm 34 is movable in a plurality of degrees of freedom to one or a plurality of orientations, relative to rail 14, stationary surgical equipment and/or subject body B in connection with a surgical procedure. In some embodiments, arm 34 is independently and selectively moveable relative to rail 14 about axis X3 to facilitate positioning of a part, such as, for example, a blade 204 (FIG. 29), as described herein.

Arm 34 includes an extension 206 and an extension 208. Extension 206 includes a tubular collar 210 that defines a socket 212 configured for disposal of ball 202. Ball 202 and collar 210 form a spheroidal joint, such as, for example, a ball joint 214 that facilitates relative movement of extension 206 and rail 14. Ball 202 is fixed with rail 14 and collar 210 is movable thereabout such that extension 206 is movable in a plurality of degrees of freedom to one or a plurality of orientations, such as, for example, poly-axial relative to rail 14, stationary surgical equipment and/or subject body B in connection with a surgical procedure. In some embodiments, ball joint 214 provides rotation of extension 206 relative to projection 200 and disposal of extension 206 at a plurality of orientations relative to axis X3. In some embodiments, extension 206 is movable relative to rail 14 between a first orientation and a second orientation in which extension 206 is moveable through an angular range relative to axis X3. In some embodiments, the orientations relative to axis X3 may include, such as, for example, transverse, perpendicular, angular orientations such as acute or obtuse, coaxial and/or may be offset or staggered.

Extension 206 includes a disc shaped collar 216 that is connected to a disc shaped collar 218 of extension 208, as described herein. Collars 216, 218 form a pivot joint 220 that is disposable between a movable orientation and a locked orientation. Pivot joint 220 defines an axis A3 disposed transverse to axis X3. Collars 216, 218 are relatively rotatable about axis A3 to facilitate rotation of extension 208 relative to extension 206 for positioning of blade 204 relative to rail 14, stationary surgical equipment and/or subject body B.

Pivot joint 220 includes a knob 222 that locks collar 216 with collar 218 such that extensions 206, 208 are disposed in a selected relative position and/or orientation relative to rail 14, stationary surgical equipment and/or subject body B. In some embodiments, knob 222 is connected with collar 216 having a radially splined surface that engages a radially splined surface of collar 218 to facilitate incremental and selective positioning of extensions 206, 208. Upon selective positioning and orientation of extensions 206, 208, knob 222 is rotated to force the splined surfaces into engagement for locking extension 206 in position with extension 208.

Extension 208 includes a tubular collar 224 that defines a socket 226. Socket 226 is configured for disposal of a bearing, such as, for example, a ball 228. Ball 228 and collar 224 form a spheroidal joint, such as, for example, a ball joint 230 that facilitates relative movement of blade 204 and extension 208. Blade 204 is movable in a plurality of degrees of freedom to one or a plurality of orientations, relative to extension 208, stationary surgical equipment and/or subject body B in connection with a surgical procedure. In some embodiments, blade 204 is independently and selectively moveable relative to extension 208 about axis X3 to facilitate positioning of blade 204, as described herein.

In some embodiments, extension 208 includes a clamp 232 for connection with blade 204. Clamp 232 is adjustable for releasable engagement with blade 204 to fix blade 204 in a selected orientation with arm 34. Clamp 232 includes a projection 234 that includes ball 228 for engagement with socket 226, as described herein, to facilitate relative movement of blade 204 and extension 208 in a plurality of degrees of freedom, such as poly-axial to one or a plurality of orientations. In some embodiments, clamp 232 includes a surface that defines a cavity (not shown) configured for disposal of an arm 204a (FIG. 29) of blade 204, as described herein. In some embodiments, clamp 232 includes a jaw (not shown) configured for translation within the cavity by actuation of a handle 236. Handle 236 is rotated such that the jaw engages arm 204a to fix blade 204 with clamp 232. In some embodiments, blade 204 in connected with a handle 238 configured to facilitate manipulation of blade 204.

In some embodiments, blade 204 is configured for disposal in a posterior orientation and engageable with tissue of a substantially posterior portion of an incision relative to subject body B, as described herein. In some embodiments, blade 204 is disposable in a configuration to space tissue of the incision to define an oblique surgical pathway P relative to a bilateral axis of subject body B, as described herein. In some embodiments, blade 204 is movable relative to extension 208 between a first orientation and a second orientation in which blade 204 is moveable through an angular range relative to extension 208. In some embodiments, blade 204 is configured to achieve a unique angle of trajectory and is unconstrained by placement of adjacent blades, as described herein. In one embodiment, blade 98 extends between a first end and a second end.

In some embodiments, blade 204 includes an outer surface configured for engaging and spacing apart tissue. Blade 204 includes an inner surface configured to define a portion of surgical pathway P. Blade 204 includes arm 204a, as shown in FIG. 29 configured for engagement with extension 208 and or an adaptor, as described herein.

In some embodiments, surgical system 10, similar to the systems and methods described herein, includes a surgical tool such as, for example, a dilator 300 configured for insertion into incision I, as shown in FIGS. 18-20. In some embodiments, surgical system 10 includes surgical instruments, such as, for example, cannulated dilators 302, 304 as shown in FIGS. 19 and 20. Dilator 300 has an outer surface 306 and includes a cylindrical cross-section configuration. Dilator 302 includes an inner surface that defines a bore 308. Bore 308 is configured for disposal of dilator 300 as dilator 302 is inserted over dilator 300. Dilator 304 includes an inner surface that defines a bore 310. Bore 310 is configured for disposal of dilator 302 as dilator 304 is inserted over dilator 302. Dilators 300, 302, 304 are configured for sequential insertion into tissue to form surgical pathway P. As shown in FIG. 21, blades 70, 72 are configured for disposal about dilator 304 to facilitate insertion of blades 70, 72 and retraction of tissue, as described herein.

In one embodiment, as shown in FIGS. 6-11, surgical system 10 includes an adaptor 430 configured for attaching a member, such as, for example, arm 32 described herein, with a part, such as, for example, blade 170. In some embodiments, adaptor 430 is configured as a quick connect attachment between arm 32 and blade 170, and resists and/or prevents toggle therebetween. In some embodiments, adaptor 430 can be employed with one or more of arms 32, 34 and blades 170, 204, as described herein. In some embodiments, adaptor 430 includes a portion of an arm of a blade, such as, for example, arm 170a and a portion of a member, such as, for example, extension 156. In some embodiments, adaptor 430 is connected with extension 156 and such connection comprises a spheroidal joint, similar to ball joint 180. In some embodiments, adaptor 430 comprises a separate component of surgical system 10 that is attached with arm 32 and blade 170.

Adaptor 430 includes a housing 432. Housing 432 is configured for a mating engagement with extension 156 of arm 32, as described herein. Housing 432 includes a surface 434 that defines a cavity 436 and a cavity 438 configured for disposal of an actuator, such as, for example, a push button 440. Cavities 436, 438 are disposed adjacent in spaced apart relation. In some embodiments, cavities 436, 438 are disposed in parallel. In some embodiments, cavities 436, 438 are disposed in various relative orientations, such as, for example, offset, staggered, transverse, perpendicular and/or angular such as obtuse or acute. Housing 432 includes a surface 442 that defines a recess 444. Recess 444 is configured for disposal of a portion of button 440 in a nested configuration in a selected position, such as, for example, an open and/or release position, as described herein.

Figure 8:
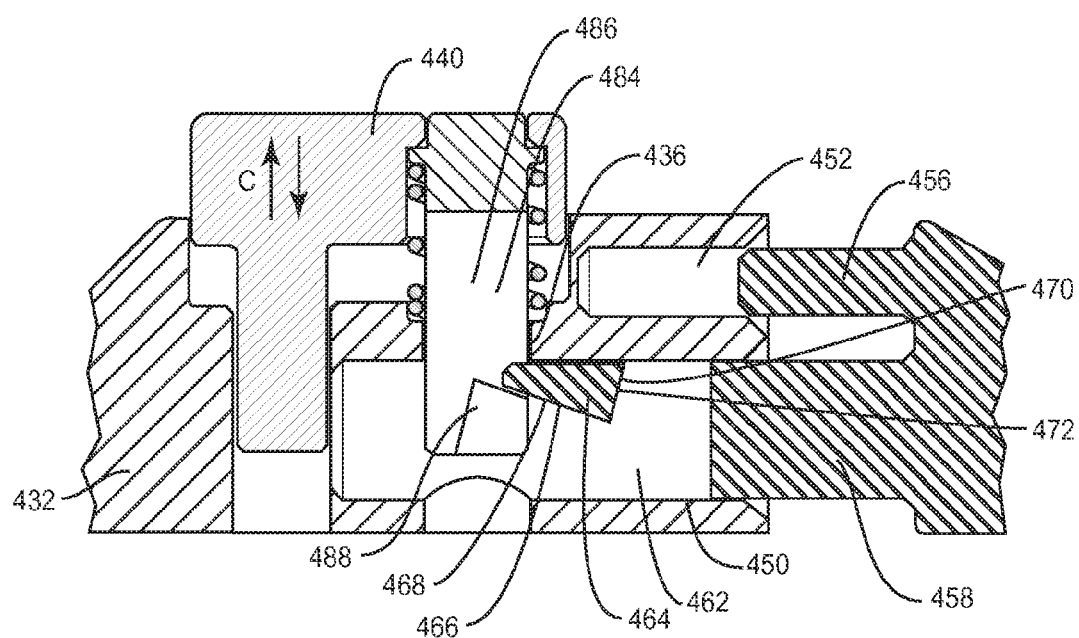
FIG. 8 is a cross section view of the components shown in FIG. 7.
Figure 9:
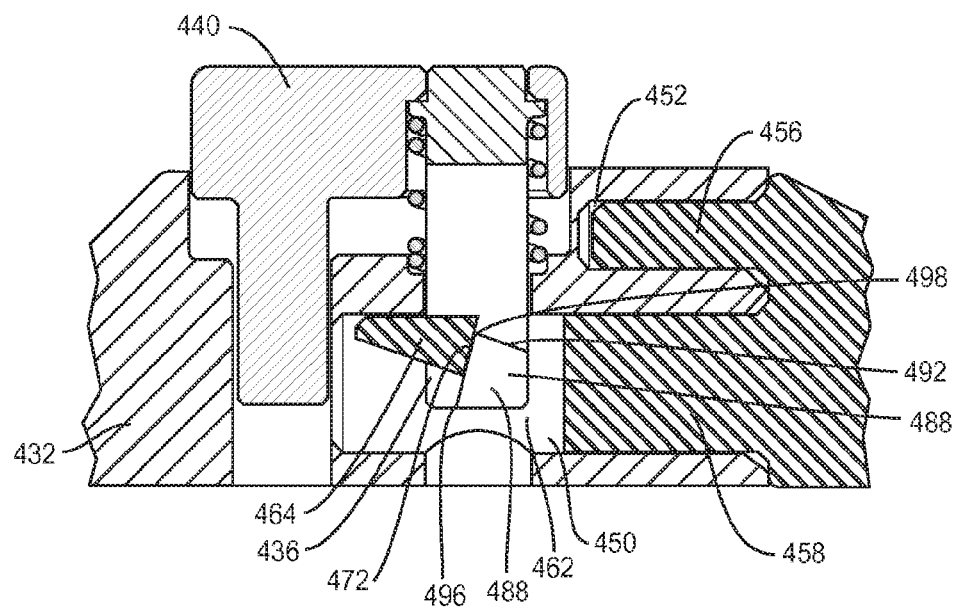
FIG. 9 is a cross section view of the components shown in FIG. 7.
Figure 10:
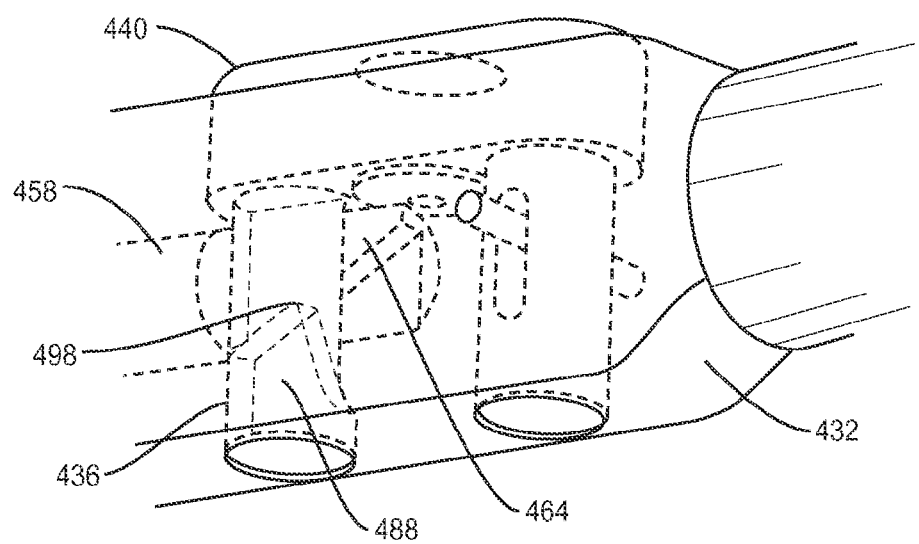
FIG. 10 is a cutaway view of the components shown in FIG. 7.
Figure 11:
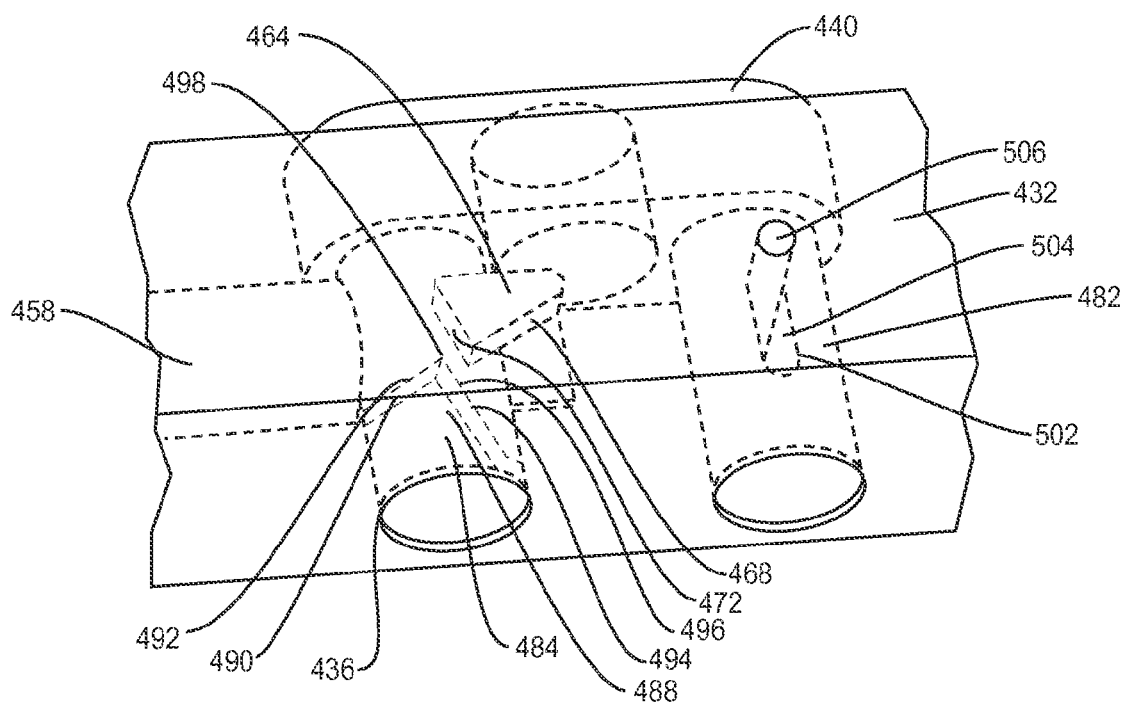
FIG. 11 is a cutaway view of the components shown in FIG. 7.

Surface 434 defines a cavity 450. Cavity 450 is disposed transverse relative to cavities 436, 438. Cavity 450 is in communication with cavity 436 to facilitate translation of arm 170a within and relative to adaptor 430 to dispose blade 170 with arm 32 between a non-locked position, as shown in FIG. 8, and a locked position, as shown in FIG. 9. Button 440 is manipulable via engagement with arm 170a and/or depressible by a practitioner for translation, in the direction shown by arrows C in FIG. 8, to dispose blade 170 with arm 32 between the non-locked position and the locked position. Surface 434 defines a cavity 452 disposed transverse relative to cavities 436, 438. Cavity 452 is configured to receive an anti-rotation element, such as, for example, a pin 456, connected with arm 170a of blade 170, as described herein.

A portion of arm 170a includes a cylinder 458 for disposal within cavity 450. Arm 170a includes a surface 460 that defines a channel 462. Surface 460 includes a wedge 464 disposed with channel 462. Wedge 464 includes a surface 466 that defines a lead ramp 468. Wedge 464 includes a surface 470 that defines a locking ramp 472. Ramps 468, 472 are configured for engagement with a wedge 488, as described herein, to facilitate translation and/or locking of blade 170 with arm 32, as described herein. Disposal of pin 456 with cavity 452 and engagement with surface 434 to resist and/or prevent rotation of arm 170a relative to extension 156.

Button 440 includes a surface 474. An extension 480 and an extension 482 extend from surface 474 into housing 432. Extension 480 is configured for disposal within cavity 436. Extension 480 includes a cylindrical portion 476. Extension 480 includes a surface 484 that defines a channel 486. Surface 484 includes a wedge 488 disposed with channel 486 and configured for engagement with wedge 464, as described herein. Wedge 488 includes a surface 490 that defines a ramp 492. Wedge 488 includes a surface 494 that defines a ramp 496. Ramps 492, 496 form an apex 498. Ramp 468 is configured for slidable engagement with ramp 492 over apex 498 to engage ramp 496 to move button 440 between a locked position and an open position, as described herein. Ramp 472 is configured for slidable engagement with ramp 496 such that adaptor 430 releasably locks blade 170 with arm 32. As ramp 472 translates along ramp 496, wedge 464 translates for disposal in a position such that wedge slides over wedge 488 and is engaged therewith in an interference fit. Spring 500, as described herein, is resiliently biased to maintain wedges 464, 488 in interference and locked orientation to resist and/or prevent arm 170a from disengaging from adaptor 430. In some embodiments, spring 500 is disposed in cavity 436 and configured to apply a force to surface 474 and wedge 464 such that arm 170a is engageable with adaptor 430 and/or button 440 is manipulable, as described herein, such that adaptor 430 is a quick release mechanism.

Extension 482 includes a surface 502 that defines a cavity 504. Cavity 504 is configured for disposal of a pin, such as, for example, an alignment pin 506 configured to facilitate alignment of button 440 with housing 432.

Figure 7:
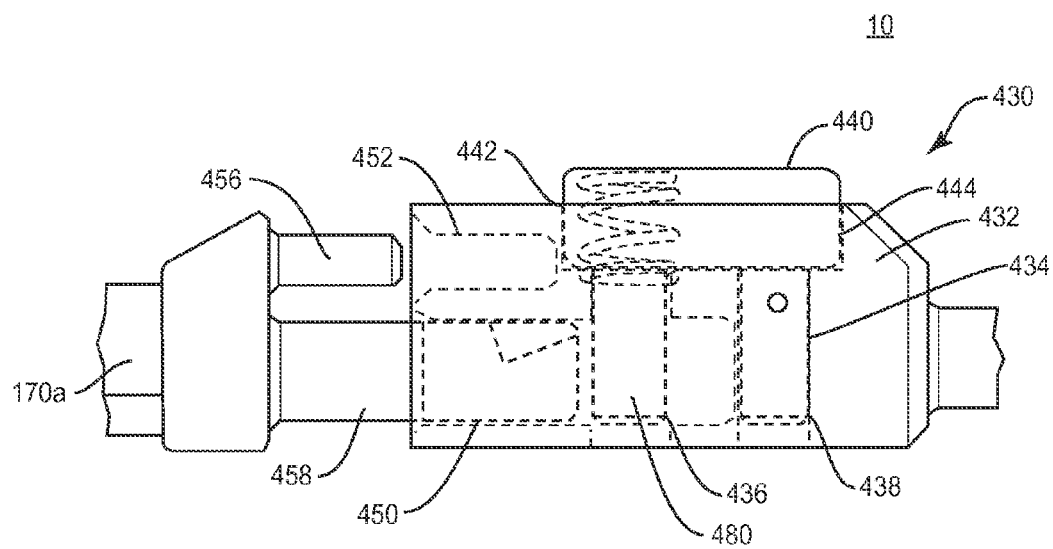
FIG. 7 is a break away side view in cutaway of components of one embodiment of a surgical system in accordance with the principles of the present disclosure.

In use, adaptor 430 is disposed in a locked position, as shown in FIG. 7, such that button 440 is nested in recess 444 and spring 500 biases button 440 in the locked position. Cylinder 458 is aligned with cavity 450 and pin 456 is aligned with cavity 452. Pin 456 and cylinder 458 are translated for disposal in cavities 450, 452 and engagement with surface 434 for connection of arm 170a with extension 156. Wedge 464 translates through channel 486 and engages wedge 488 such that button 440 translates and the bias force of spring 500 is overcome, as shown in FIG. 8. Translation of wedge 464 through channel 486 causes ramp 168 to translate along ramp 192 to apex 198. Ramp 168 slides over apex 198 to engage ramp 496. Wedge 464 is disposed in a position such that wedge 464 slides over wedge 488 and is engaged therewith in an interference fit. Spring 500 expands to the resiliently biased orientation to maintain wedges 464, 488 in interference and locked orientation to resist and/or prevent arm 170a from disengaging from adaptor 430, as shown in FIG. 9. In some embodiments, adaptor 430 is configured as a quick connect attachment between arm 32 and blade 170, and resists and/or prevents toggle therebetween.

Figure 12:
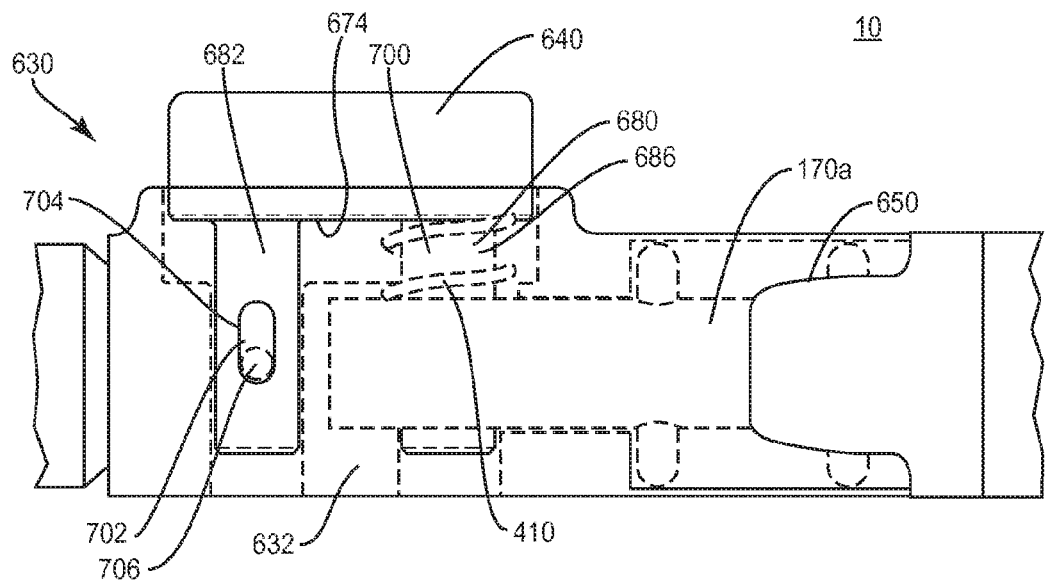
FIG. 12 is a break away side view in cutaway of components of one embodiment of a surgical system in accordance with the principles of the present disclosure.
Figure 13:
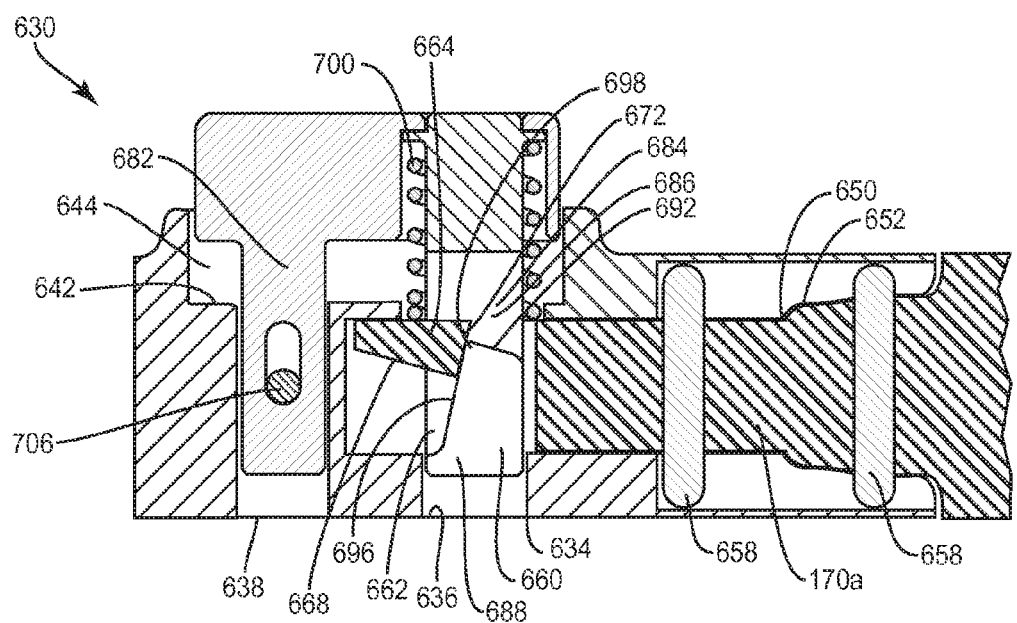
FIG. 13 is a cross section view of the components shown in FIG. 12.

In one embodiment, as shown in FIGS. 12 and 13, surgical system 10, similar to the systems and methods described herein, includes an adaptor 630, similar to adaptor 430 described herein, for attaching a member, such as, for example, arm 32 described herein, with a part, such as, for example, blade 170.

Adaptor 630 includes a housing 632. Housing 632 is configured for a mating engagement with extension 156 of arm 32, as described herein. Housing 632 includes a surface 634 that defines a cavity 636 and a cavity 638 configured for disposal of a push button 640, similar to button 440 described herein. Cavities 636, 638 are disposed adjacent in spaced apart relation. Housing 632 includes a surface 642 that defines a recess 644. Recess 644 is configured for disposal of a portion of button 640 in a nested configuration in a selected position, such as, for example, an open and/or release position, as described herein.

Housing 632 includes a cavity 650 disposed transverse to cavities 636, 638. Cavity 650 is in communication with cavity 636 to facilitate translation of arm 170a within and relative to adaptor 630 to dispose blade 170 with arm 32 between a non-locked position and a locked position. Cavity 650 includes a tapered surface 652. Tapered surface 652 is configured to form a friction fit with a surface of arm 170a, as described herein. Arm 170a includes a tapered configuration and is configured for disposal within cavity 650 in a friction fit configuration. The friction fit of arm 170a and surface 652 resists and/or prevents rotation of arm 170a relative to extension 156. In some embodiments, arm 170a is configured for engagement with dowel pins 658 that are configured to facilitate alignment and isolate rotational loads.

Button 640 is manipulable via engagement with arm 170a and/or depressible by a practitioner for translation to dispose blade 170 with arm 32 between the non-locked position and the locked position. Arm 170a includes a surface 660 that defines a channel 662. Surface 660 includes a wedge 664 disposed with channel 662. Wedge 664 includes a lead ramp 668. Wedge 664 includes a locking ramp 672. Ramps 668, 672 are configured for engagement with a wedge 688, as described herein, to facilitate translation and/or locking of blade 170 with arm 32, as described herein.

Button 640 includes a surface 674. An extension 680 and an extension 682 extend from surface 674 into housing 632. Extension 680 is configured for disposal within cavity 636. Extension 680 includes a cylindrical portion 676. Extension 680 includes a surface 684 that defines a channel 686. Surface 684 includes a wedge 688 disposed with channel 686 and configured for engagement with wedge 664, as described herein. Wedge 688 defines a ramp 692. Wedge 688 defines a ramp 696. Ramps 692, 696 form an apex 698. Ramp 668 is configured for slidable engagement with ramp 692 over apex 698 to engage ramp 696 to move button 640 between a locked position and an open position, as described herein. Ramp 672 is configured for slidable engagement with ramp 696 such that adaptor 630 releasably locks blade 170 with arm 32. As ramp 672 translates along ramp 696, wedge 664 translates for disposal in a position such that wedge slides over wedge 688 and is engaged therewith in an interference fit. Spring 700, as described herein, is resiliently biased to maintain wedges 664, 688 in interference and locked orientation to resist and/or prevent arm 170a from disengaging from adaptor 630. In some embodiments, spring 700 is disposed in cavity 636 and configured to apply a force to surface 674 and wedge 664 such that arm 170a is engageable with adaptor 630 and/or button 640 is manipulable, as described herein, such that adaptor 630 is a quick release mechanism.

Extension 682 includes a surface 702 that defines a cavity 704. Cavity 704 is configured for disposal of a pin, such as, for example, an alignment pin 706 configured to facilitate alignment of button 640 with housing 632.

Figure 14:
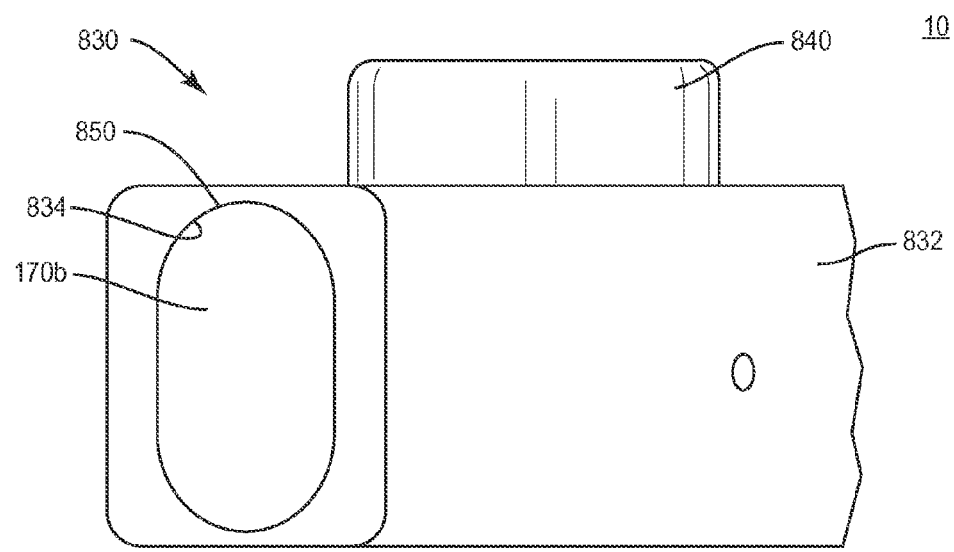
FIG. 14 is a break away perspective view of components of one embodiment of a surgical system in accordance with the principles of the present disclosure.
Figure 15:
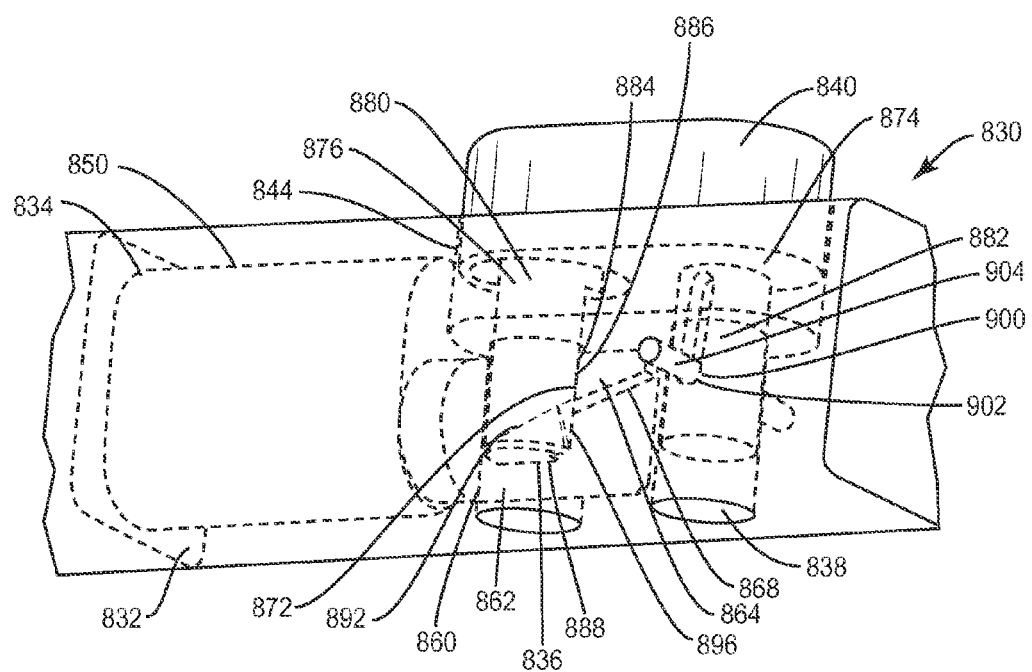
FIG. 15 is a cutaway view of the components shown in FIG. 14.

In one embodiment, as shown in FIGS. 14 and 15, surgical system 10, similar to the systems and methods described herein, includes an adaptor 830, similar to adaptor 630 described herein, for attaching a member, such as, for example, arm 32 described herein, with a part, such as, for example, blade 170 that includes an arm 170b, similar to arm 170a, having an oval cross section configuration.

Adaptor 830 includes a housing 832. Housing 832 is configured for a mating engagement with extension 156 of arm 32, as described herein. Housing 832 defines a cavity 836 and a cavity 838 for disposal of a push button 840, similar to button 640 described herein. Housing 832 defines a recess 844 for disposal of a portion of button 840 in an open and/or release position, as described herein.

Housing 832 includes surface 834 that defines a cavity 850 disposed transverse to cavities 836, 838. Cavity 850 is in communication with cavity 836 to facilitate translation of arm 170b within and relative to adaptor 830 to dispose blade 170 with arm 32 between a non-locked position and a locked position. Cavity 850 has an oval cross section configuration. Arm 170b is configured for disposal within cavity 850 such that surface 834 engages a surface of arm 170b in an interference fit to resist and/or prevent rotation of arm 170b relative to extension 156.

Button 840 is manipulable via engagement with arm 170b and/or depressible by a practitioner for translation to dispose blade 170 with arm 32 between the non-locked position and the locked position. Arm 170b includes a surface 860 that defines a channel 862. Surface 860 includes a wedge 864 disposed with channel 862. Wedge 864 includes a lead ramp 868. Wedge 864 includes a locking ramp 872. Ramps 868, 872 are configured for engagement with a wedge 888, as described herein, to facilitate translation and/or locking of blade 170 with arm 32, as described herein.

Button 840 includes a surface 874. An extension 880 and an extension 882 extend from surface 874 into housing 832. Extension 880 is configured for disposal within cavity 836. Extension 880 includes a cylindrical portion 876. Extension 880 includes a surface 884 that defines a channel 886. Surface 884 includes a wedge 888 disposed with channel 886 and configured for engagement with wedge 864, as described herein. Wedge 888 defines a ramp 892. Wedge 888 defines a ramp 896. Ramps 892, 896 form an apex. Ramp 868 is configured for slidable engagement with ramp 892 over the apex to engage ramp 896 to move button 840 between a locked position and an open position, similar to that described herein. Ramp 872 is configured for slidable engagement with ramp 896 such that adaptor 830 releasably locks blade 170 with arm 32. Extension 882 includes a surface 900 that defines a cavity 902. Cavity 902 is configured for disposal of an alignment pin 904.

Figure 16:
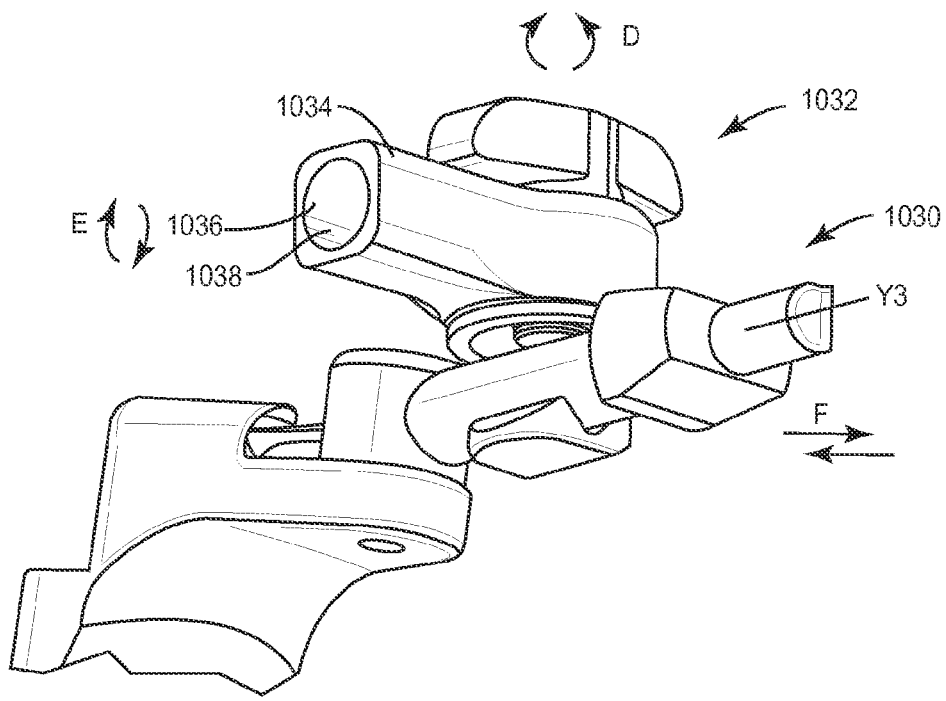
FIG. 16 is a break away perspective view of components of one embodiment of a surgical system in accordance with the principles of the present disclosure.
Figure 17:
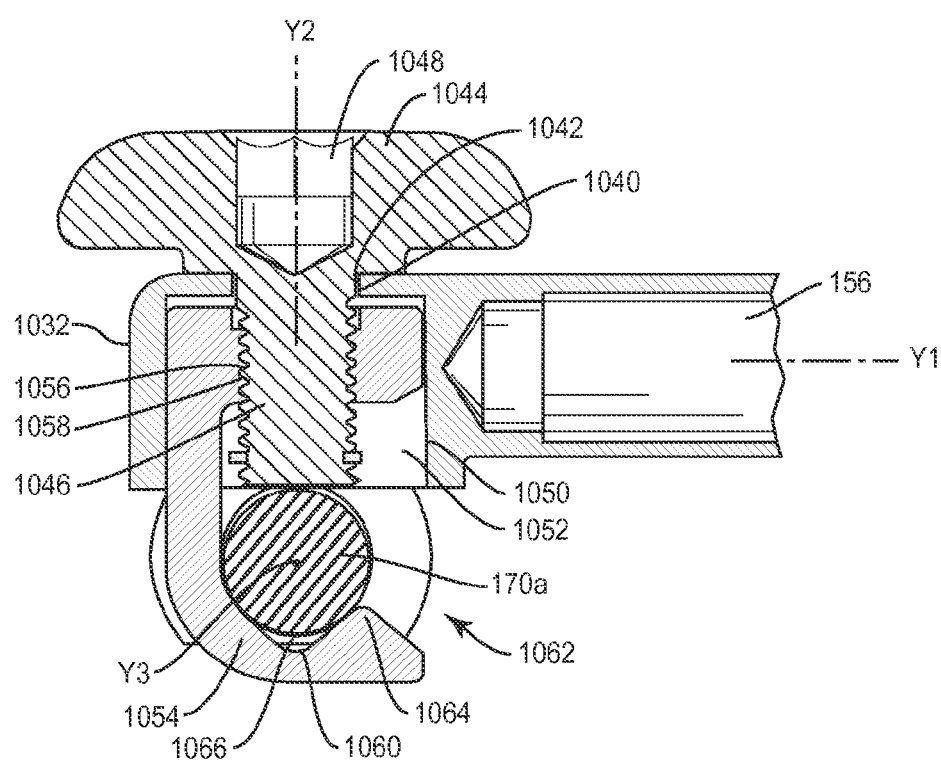
FIG. 17 is a cross section view of the components shown in FIG. 16.

In some embodiments, as shown in FIGS. 16 and 17, surgical system 10 includes an adaptor 1030 configured for attaching a member, such as, for example, arm 32 described herein, with a part, such as, for example, blade 170. In some embodiments, adaptor 1030 can be employed with one or more of arms 32, 34 and blades 170, 204, as described herein. In some embodiments, adaptor 1030 includes a portion of an arm of a blade, such as, for example, arm 170a and a portion of a member, such as, for example, extension 156. In some embodiments, adaptor 1030 is connected with extension 156 and such connection comprises a spheroidal joint, similar to ball joint 180. In some embodiments, adaptor 1030 comprises a separate component of surgical system 10 that is attached with arm 32 and blade 170.

Adaptor 1030 connects arm 32 with blade 170 and facilitates relative movement of arm 170a and extension 156. In some embodiments, adaptor 1030 connects arm 32 with blade 170 such that blade 170 is movable to one or a plurality of degrees of freedom, as described with regard to retractor 12 herein, to one or a plurality of orientations relative to rail 14, stationary surgical equipment and/or subject body B in connection with a surgical procedure. In some embodiments, adaptor 1030 connects arm 32 with blade 170 such that blade 170 is movable to a plurality of degrees of freedom including two degrees of freedom in rotation and one degrees of freedom in translation, relative to extension 156. In some embodiments, adaptor 1030 connects arm 32 with blade 170 such that blade 170 is independently and selectively moveable relative to arm 32 to facilitate positioning of blade 170, as described herein.

Adaptor 1030 includes a collar 1032. Collar 1032 includes an extension 1034 having a surface 1036 defining an opening 1038 configured for disposal of extension 156. Extension 1034 defines an axis Y1. In some embodiments, surface 1036 and a surface of extension 156 comprise a spheroidal joint, similar to ball joint 180.

Collar 1032 includes a surface 1040 that defines an opening 1042 for disposal of a handle 1044 having a threaded shaft 1046. Handle 1044 includes a socket 1048 having a hexalobe geometry configured for disposal of a similarly shaped bit of a tool, such as, for example, a driver (not shown) to engage handle 1044 to rotate shaft 1046. In some embodiments, socket 1048 has a cruciform, phillips, square, hexagonal, polygonal, star cross sectional configuration configured for disposal of a correspondingly shaped portion of a driver.

Collar 1032 includes an inner surface 1050 that defines a cavity 1052 configured for disposal of a jaw 1054. Jaw 1054 includes an inner surface 1056 that defines a threaded passageway 1058 configured for disposal and threaded fixation with shaft 1046. Jaw 1054 is engageable with handle 1044 in threaded fixation to dispose blade 170 with arm 32 between a non-locked position and a locked position. Shaft 1046 is engaged with jaw 1054 to define an axis Y2.

Jaw 1054 includes a surface 1060 that defines a cavity, such as, for example, a lateral passageway 1062. Passageway 1062 is configured for disposal of arm 170a, which define an axis Y3. Surface 1060 includes a retaining flange 1064. Flange 1064 defines a recess 1066 with surface 1060 configured for disposal of arm 170a. In some embodiments, flange 1064 is oriented in a snap fit configuration to retain arm 170a with adaptor 1030. In some embodiments, adaptor 1030 includes a spring (not shown) disposed within cavity 1052 to bias adaptor 1030 in a provisionally closed or locked position with arm 170a to retain arm 170a with adaptor 1030 prior to fixation of arm 32 in a final orientation. In some embodiments, the provisionally closed or locked position includes jaw 1054 being biased and/or drawn upwardly with arm 170a relative to cavity 1052. In some embodiments, the spring (not shown) is disposed about shaft 1046. In some embodiments, the spring (not shown) is disposed between jaw 1054 and surface 1050.

Adaptor 1030 connects arm 32 with blade 170 such that blade 170 is movable to a plurality of degrees of freedom. Adaptor 1030 is fixed with extension 156. Arm 170a is disposed with passageway 1062. Adaptor 1030 is spring preloaded to bias handle 1044 and/or jaw 1054 to a provisionally closed or locked position with arm 170a to retain arm 170a with adaptor 1030 prior to fixation of arm 32 in a final orientation.

Arm 170a is movable to at least three additional degrees of freedom as facilitated by adaptor 1030 including two degrees of freedom in rotation and one degree of freedom in translation, relative to extension 156. Arm 170a is rotatable relative to and about axis Y2, in the direction shown by arrows D in FIG. 16, rotatable relative to and about axis Y3, in the direction shown by arrows E, and translatable relative to and along axis Y3, in the direction shown by arrows F, to a selected orientation relative to extension 156. Upon positioning of blade 170 relative to extension 156 in a selected orientation, as described herein, a driver is engaged with socket 1048 and/or handle 1044 is manipulated to rotate shaft 1046 in threaded engagement with jaw 1054. Shaft 1046 engages arm 170a to lock blade 170 in the selected orientation with extension 156.

In some embodiments, surgical system 10 may comprise various surgical instruments, such as, for example, drivers, extenders, reducers, spreaders, distractors, clamps, forceps, elevators and drills, which may be alternately sized and dimensioned, and arranged as a kit. In some embodiments, surgical system 10 may comprise the use of microsurgical and image guided technologies, such as, for example, surgical navigation components employing emitters and sensors, which may be employed to track introduction and/or delivery of the components of surgical system 10 including the surgical instruments to a surgical site. See, for example, the surgical navigation components and their use as described in U.S. Pat. Nos. 6,021,343, 6,725,080 and 6,796,988, the entire contents of each of these references being incorporated by reference herein.

In assembly, operation and use, as shown in FIGS. 18-30, surgical system 10, similar to the systems described herein, is employed with a surgical procedure for treatment of a spinal disorder, such as those described herein, affecting a section of a spine of a patient. Surgical system 10 may also be employed with other surgical procedures. To treat the affected section of vertebrae of a subject body, the subject body is disposed in a side orientation relative to a surgical fixed surface, such as, for example, a surgical table configured for supporting the subject body.

The subject body B is oriented such that an OLIF procedure can be performed obliquely in front of a psoas muscle to provide direct access to one or more intervertebral spaces of L2-L5 vertebral levels of the vertebrae while avoiding selected muscular and abdominal anatomical structures, such as, for example anterior vasculature. In some embodiments, placement of the subject body on its side facilitates access to surgical pathway P that is disposed at an oblique angle. In some embodiments, placement of the subject body on its side facilitates natural movement of the abdominal contents away from surgical pathway P via the effect of gravity.

In some embodiments, psoas muscle is completely paralyzed during the surgical procedure as there is no need to monitor or locate nerves present in psoas muscle PM as psoas muscle is avoided along the oblique surgical pathway P. In some embodiments, paralyzing psoas muscle facilitates manipulation and/or retraction of psoas muscle during the surgical procedure.

The L2 and L5 disc spaces, lower ribs and iliac crest can be marked on the skin as landmarks. In some embodiments, for example, in a single vertebral level procedure, the subject body is marked 4-10 centimeters (cm) anterior to the midsection of the target disc (or approximately one third of the distance from the top of the iliac crest to the umbilicus). A 3 cm to 6 cm vertical, horizontal or oblique incision is made in tissue of the subject body. In some embodiments, for example, in a two vertebral level procedure, the subject body is marked 4-10 cm anterior to the midsection of the intervening vertebral body and an incision is made in tissue of the subject body. In one embodiment, the lumbar lordosis of the operative levels can be marked on the skin to determine the angle in line with the disc space.

In some embodiments, the subcutaneous fat layers are dissected until the abdominal musculature is reached. In some embodiments, a mono-polar cautery can be utilized for hemostasis, and a small self-retaining retractor can be used for initial dissection of the skin and subcutaneous layer. In some embodiments, the external oblique fascia is the first plane encountered and is the only layer that will need to be sharply incised. In some embodiments, a clamp is used to bluntly spread through the fibers of the external oblique, internal oblique, and transversalis muscles. In some embodiments, dissection is performed in line with the muscle fibers as these muscle layers extend in opposite directions.

In some embodiments, an index finger is utilized to follow the internal abdominal wall posteriorly down to the psoas muscle. In some embodiments, a finger or a blunt instrument is used to sweep the peritoneal contents, including the ureter, which reflects with the peritoneum, and the retroperitoneal fat anteriorly past the anterior portion of psoas muscle PM clearing to the anterior vertebral body.

Dilator 300 is initially inserted into incision I along an oblique trajectory along surgical pathway P, as shown in FIG. 18, anterior relative to the psoas muscle and posterior to a peritoneum (not shown). Dilator 302 is inserted over dilator 300, as shown in FIG. 19, in a telescoping configuration. In some embodiments, dilator 302 is disposed for a centered alignment over dilator 300. Dilator 304 is inserted over dilator 302, as shown in FIG. 20, in a telescoping configuration. In some embodiments, dilator 304 is disposed for a centered alignment over dilator 302.

A surgical instrument, such as, for example, retractor 12, as described herein, is disposed with incision I and in communication with surgical pathway P for spacing tissue. Retractor blades 70, 72, 170 and 204, as described herein, are configured for insertion sequentially around the L2-L5 intervertebral space to protect tissue and/or vessels, as described herein. Rail 14 is attached to surgical equipment, as described herein. In some embodiments, an adaptor, such as, for example, adaptor 1030 is attached with arms 32 and/or 34 and blades 170 and/or 204, similar to that described herein.

Figure 22:
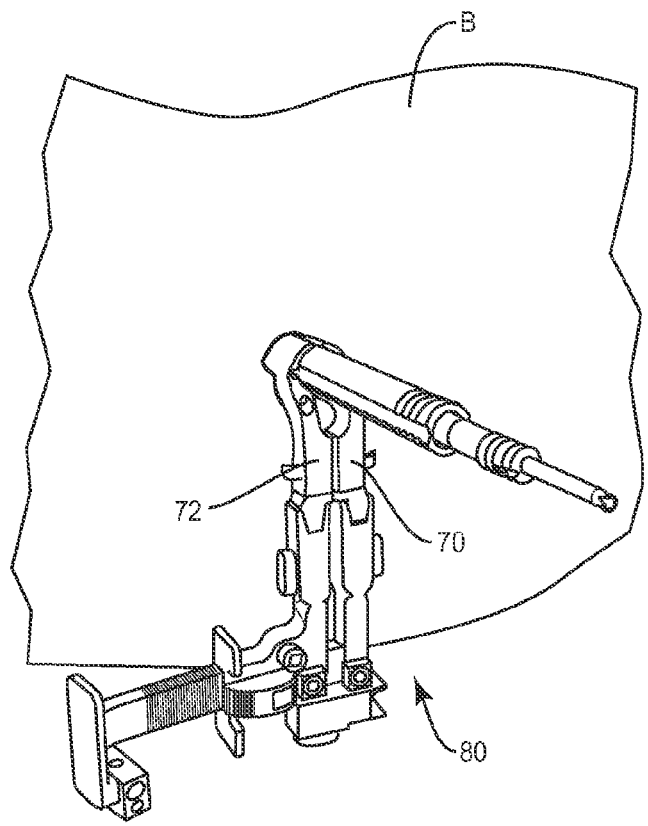
FIG. 22 is a perspective view of components of one embodiment of a system in accordance with the principles of the present disclosure disposed with a patient body.
Figure 23:
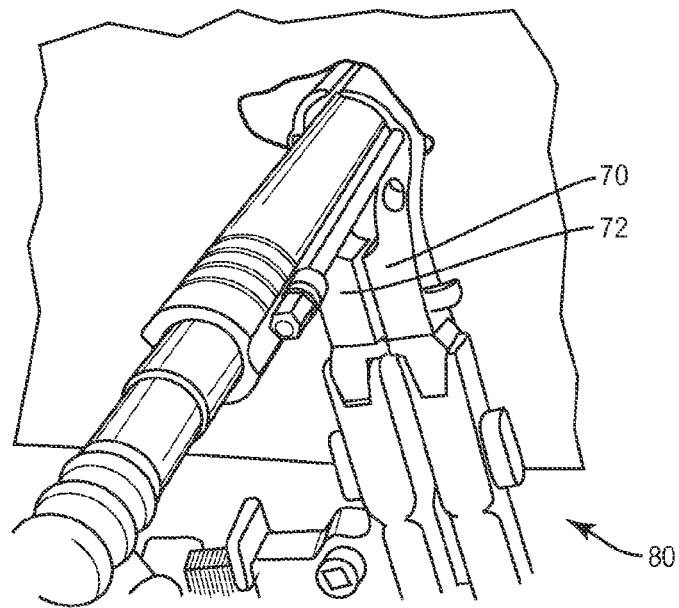
FIG. 23 is a perspective view of components of one embodiment of a system in accordance with the principles of the present disclosure disposed with a patient body.
Figure 24:
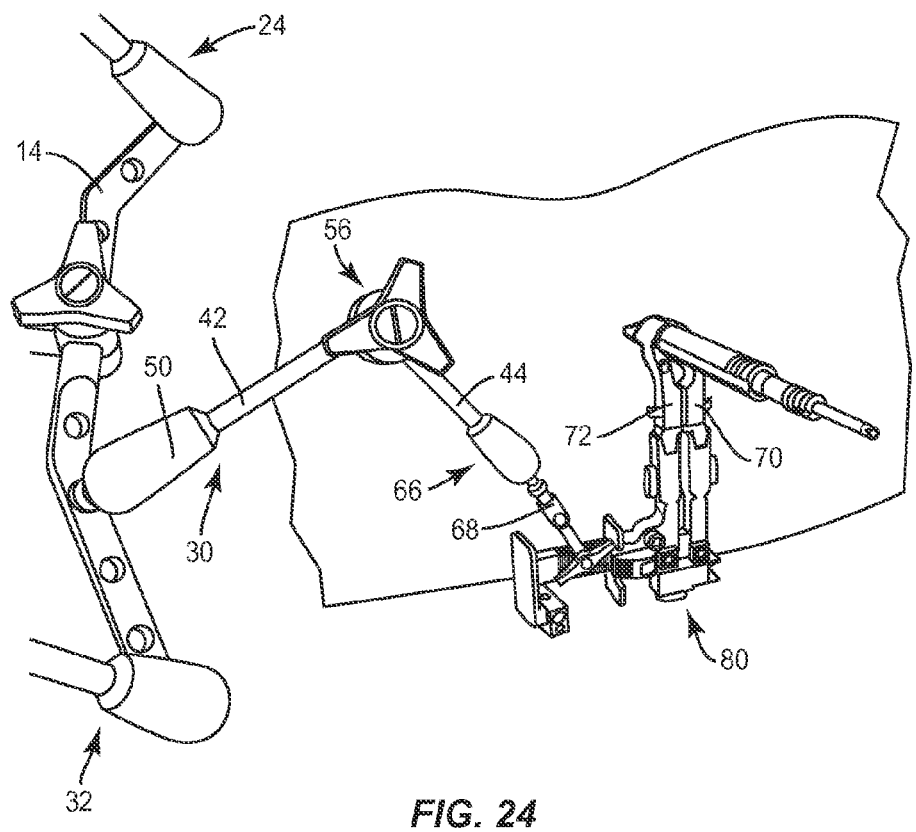
FIG. 24 is a perspective view of components of one embodiment of a system in accordance with the principles of the present disclosure disposed with a patient body.

Rack retractor assembly 80, as described herein, and blades 70, 72 are attached with arm 30. Rack retractor assembly 80 and blades 70, 72 are manipulated into alignment with dilator 304 by arm 30. Blades 70, 72 are moveable to one or a plurality of orientations, relative to rail 14, arm 30, stationary surgical equipment and/or tissue of subject body B adjacent the surgical site in connection with a surgical procedure. Blades 70, 72 are disposed in a closed configuration and in a position, as shown in FIGS. 21 and 22, such that blades 70, 72 are introduced along an oblique trajectory along surgical pathway P over dilator 304 in a cranial-caudal orientation relative to body B. Dilators 300, 302, 304 are removed from incision I. Blades 70, 72 are manipulated by rack retractor assembly 80 into an open position, as shown in FIG. 25. Blade 70 is translated relative to blade 72 to space tissue in the cranial-caudal orientation relative to body B.

Figure 28:
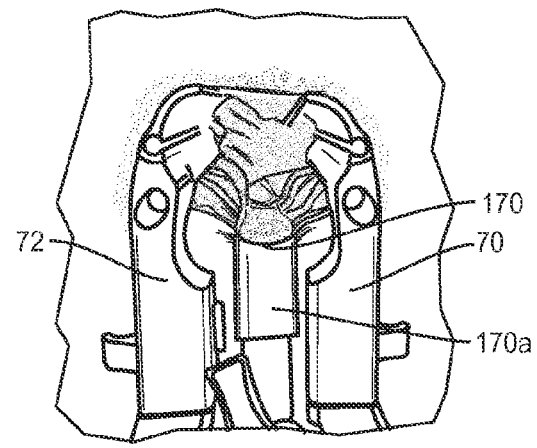
FIG. 28 is a side view of components of one embodiment of a system in accordance with the principles of the present disclosure disposed with a patient body.

Blade 170 is movable in a plurality of degrees of freedom to one or a plurality of orientations, relative to rail 14, arm 32, stationary surgical equipment and/or tissue of subject body B adjacent the surgical site in connection with a surgical procedure. Blade 170 is manipulated for movement, as described herein, via adaptor 1030 and/or arm 32 relative to incision I to align and guide blade 170 into an anterior orientation and/or engagement with an anterior portion of incision I relative to body B, as shown in FIG. 28.

Blade 204 is movable in a plurality of degrees of freedom to one or a plurality of orientations, relative to rail 14, arm 34, stationary surgical equipment and/or tissue of subject body B adjacent the surgical site in connection with a surgical procedure. Blade 204 is manipulated for movement, as described herein, via adaptor 1030 and/or arm 34 relative to incision I to align and guide blade 204 into a posterior orientation and/or engagement with a posterior portion of incision I relative to body B, as shown in FIG. 30. Retractor 12 spaces tissue adjacent incision I to define surgical pathway P, which allows for instruments and/or implants to be inserted into body B obliquely through surgical pathway P.

In some embodiments, a discectomy is performed via surgical pathway P. In some embodiments, instruments, such as, for example, a Cobb elevator, mallet, shaver, serrated curettes, rasp, a ring curette, a uterine curette and/or a combination thereof are utilized to perform a discectomy of the disc space.

In some embodiments, an anterior longitudinal ligament (ALL) release procedure can be performed using an OLIF approach post-discectomy. For example, loosening the ALL can be performed by placing holes or partial cuts in the ALL such that the OLIF surgical pathway is immediately closer to the ALL.

In some embodiments, trial implants (not shown) are delivered along surgical pathway P. The trial implants are used to distract one or more intervertebral spaces of the L2-L5 vertebral levels and apply appropriate tension in the intervertebral space allowing for indirect decompression. In one embodiment, a direct decompression of the disc space is performed by removing a portion of a herniated disc. In some embodiments, one or a plurality of interbody implants can be introduced and delivered along surgical pathway P for implantation with one or more intervertebral spaces of the L2-L5 vertebral levels.

In some embodiments, pilot holes or the like are made in the vertebrae adjacent its intervertebral space, via surgical pathway P for receiving bone fasteners and/or attaching spinal constructs, which may include rods and plates. An inserter is attached with the implants and/or spinal constructs for delivery along surgical pathway P adjacent to a surgical site for implantation adjacent one or more vertebra and/or intervertebral spaces of the L2-L5 vertebral levels.

Upon completion of a procedure, as described herein, the surgical instruments, assemblies and non-implanted components of surgical system 10 are removed and the incision(s) are closed. One or more of the components of surgical system 10 can be made of radiolucent materials such as polymers. Radiopaque markers may be included for identification under x-ray, fluoroscopy, CT or other imaging techniques. In some embodiments, the use of surgical navigation, microsurgical and image guided technologies, as described herein, may be employed to access, view and repair spinal deterioration or damage, with the aid of surgical system 10. In some embodiments, surgical system 10 may include implants and/or spinal constructs, which may include one or a plurality of plates, rods, connectors and/or bone fasteners for use with a single vertebral level or a plurality of vertebral levels.

In one embodiment, surgical system 10 includes an agent, which may be disposed, packed, coated or layered within, on or about the components and/or surfaces of surgical system 10. In some embodiments, the agent may include bone growth promoting material, such as, for example, bone graft allograft, xenograft, autograft, bone paste, bone chips, Skelite®, and/or BMP to enhance fixation of the components and/or surfaces of surgical system 10 with vertebrae. In some embodiments, the agent may include one or a plurality of therapeutic agents and/or pharmacological agents for release, including sustained release, to treat, for example, pain, inflammation and degeneration. In such embodiments, titanium coatings may be applied via a variety of methods, including but not limited to plasma spray coating and/or mechanical attachment of titanium plates to form a PEEK/Titanium implant.

Figure 31:
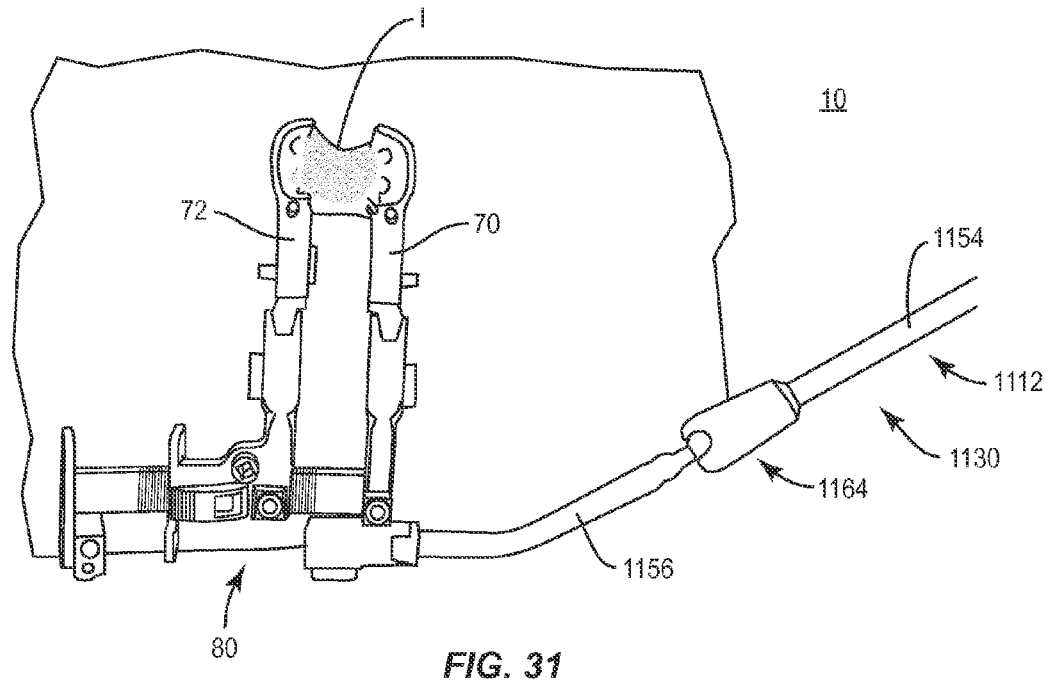
FIG. 31 is a plan view of components of one embodiment of a system in accordance with the principles of the present disclosure disposed with a patient body.
Figure 32:
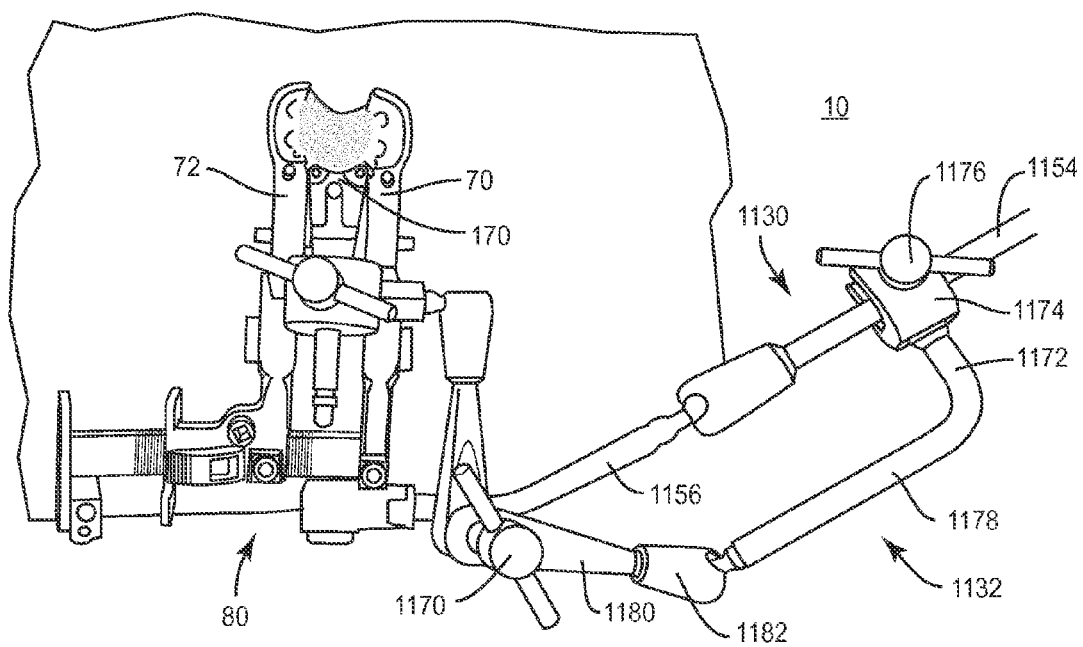
FIG. 32 is a plan view of components of one embodiment of a system in accordance with the principles of the present disclosure disposed with a patient body.
Figure 33:
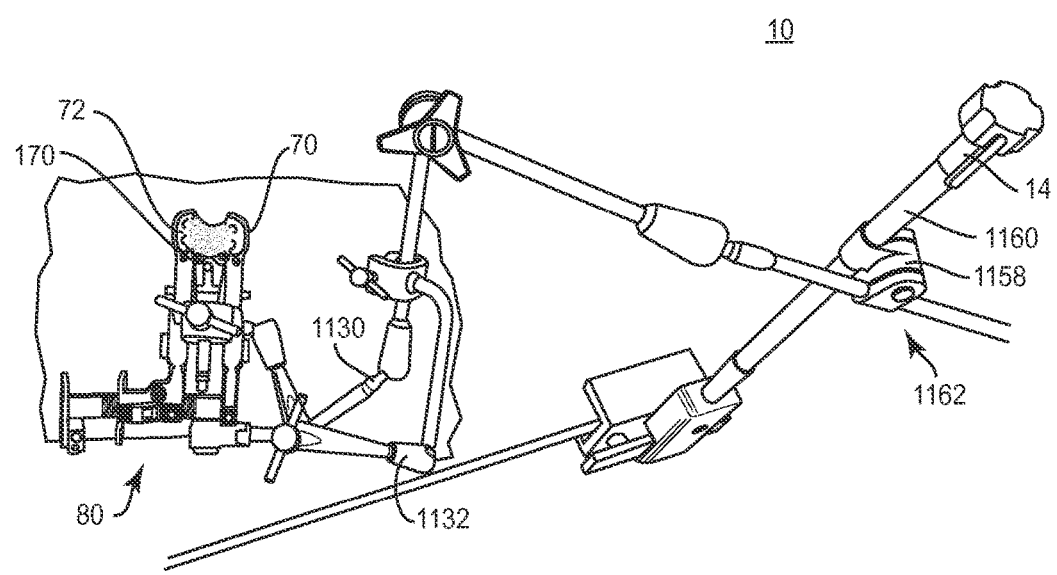
FIG. 33 is a perspective view of components of one embodiment of a system in accordance with the principles of the present disclosure disposed with a patient body.

In one embodiment, as shown in FIGS. 31-33, surgical system 10, similar to the systems and methods described herein, comprises surgical retractor 1112, similar to retractor 12, described herein. Surgical retractor 1112 includes rack retractor assembly 80 and blades 70, 72, described herein, attached to an arm 1130, similar to arm 30, and blade 170, described herein, attached to an arm 1134, similar to arm 34 described herein.

Arm 1130 includes extension 1154 and extension 1156. Extension 1154 is configured for pivotable connection with rail 14 by a collar 1158 and a collar 1160 forming a pivot joint 1162. Extension 1156 is configured for connection with rack retractor assembly 80, as shown in FIG. 31. Extension 1154 is connected to extension 1156 via a spheroidal joint, such as, for example, a ball joint 1164, similar to ball joint 180 described herein. Ball joint 1164 is configured to provide freedom of movement and/or toggle of extension 1156 relative to extension 1154. Arm 1130 is movable in a plurality of degrees of freedom to one or a plurality of orientations, relative to a rail 14, stationary surgical equipment and/or subject body B in connection with a surgical procedure. In some embodiments, arm 1130 is independently and selectively moveable relative to rail 14 to facilitate positioning of a part, such as, for example, blades 70, 72, as described herein.

An arm 1132, similar to arm 32 described herein, is configured for attachment with arm 1130. Arm 1132 is configured for independent and selective movement relative to arm 1130. Arm 1132 extends between an end 1170 and an end 1172. End 1172 is configured for attachment to arm 1130 by a clamp 1174 such that arm 1132 is translatable along arm 1130. Clamp 1174 includes a handle 1176 configured to facilitate translation along arm 1130 and fixation of arm 1132 relative to arm 1130.

Arm 1132 includes an extension 1178 and an extension 1180. Extension 1178 extends from clamp 1174 is angular orientation, such as, for example, perpendicular. Extension 1180 extends from extension 1178 to facilitate placement of a blade 170 anteriorly relative to a patient body B, as shown in FIG. 32. In some embodiments, all or only a portion of extension 1178 may extend in alternate configurations from clamp 1174, such as, for example, offset, serial, staggered, transverse and/or parallel.

Extension 1180 is connected to extension 1178 via a spheroidal joint, such as, for example, a ball joint 1182, similar to ball joint 180 described herein. Ball joint 1182 is configured to provide freedom of movement and/or toggle of extension 1180 relative to extension 1178. Arm 1132 is movable in a plurality of degrees of freedom to one or a plurality of orientations, relative to a rail 14, stationary surgical equipment and/or subject body B in connection with a surgical procedure. In some embodiments, arm 1132 is independently and selectively moveable relative to rail 14 to facilitate positioning of a part, such as, for example, blade 170, as described herein.

In operation, rack retractor assembly 80 and blades 70, 72 are attached with arm 1130. Rack retractor assembly 80 and blades 70, 72 are manipulated into alignment and are moveable to one or a plurality of orientations, relative to rail 14, arm 1130, stationary surgical equipment and/or tissue of subject body B adjacent the surgical site in connection with a surgical procedure. Blades 70, 72 are disposed in a closed configuration with an incision, similar to that described herein. Blades 70, 72 are manipulated by rack retractor assembly 80 into an open position such that blade 70 is translated relative to blade 72 to space tissue in the cranial-caudal orientation relative to body B, as shown in FIG. 31.

Blade 170 is movable in a plurality of degrees of freedom to one or a plurality of orientations, relative to rail 14, arm 1132, stationary surgical equipment and/or tissue of subject body B adjacent the surgical site in connection with a surgical procedure. Blade 170 is manipulated for movement, as described herein, relative to incision I to align and guide blade 170 into an anterior orientation and/or engagement with an anterior portion of incision I relative to body B. In some embodiments, a posterior blade, similar to blade 204, may be disposed with incision I, similar to that described herein.

It will be understood that various modifications and/or combinations may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A surgical instrument comprising:
    an element connectable with a fixture;
    a first member independently and selectively movable relative to the element and including a part engageable with an incision in a cranial-caudal orientation relative to a body to space apart tissue, the part comprising a housing having a first blade and a shaft disposed in the housing, the shaft including an arm and a second blade that is coupled to the arm, the shaft defining a longitudinal axis, the second blade being coupled to the shaft such that the second blade is prevented from translating relative to the shaft along the longitudinal axis, the arm including a flange and a lever that is pivotable relative to the flange to facilitate rotation of the arm about an axis defined by the arm;
    a second member independently and selectively movable relative to the element and including a part engageable with tissue of an anterior portion of the incision; and
    a third member independently and selectively movable relative to the element and including a part engageable with tissue of a posterior portion of the incision,
    wherein the parts are disposable in a configuration to space tissue of the incision to define an oblique surgical pathway relative to a bilateral axis of the body, the element comprising a collar having a splined surface that rotatably engages a splined surface of a collar of the fixture to simultaneously rotate the members relative to the fixture.

2. A surgical instrument as recited in claim 1, wherein the first blade is coupled to the housing by the arm.

3. A surgical instrument as recited in claim 1, wherein the second blade is coupled to the shaft by a second arm, the second arm being rotatable relative to the shaft, the second arm including a second flange and a second lever that is pivotable relative to the second flange to facilitate rotation of the second arm about an axis defined by the second arm.

4. A surgical instrument as recited in claim 1, wherein the housing comprises a lock configured to engage teeth of the shaft to selectively space the blades apart.

5. A surgical instrument as recited in claim 4, wherein the lock is pivotable about a pivot axis that extends transverse to the shaft.

6. A surgical instrument as recited in claim 1, wherein the first blade includes an inner surface and the second blade includes an inner surface, the inner surfaces define a substantially oval cavity.

7. A surgical instrument as recited in claim 1, wherein at least one of the members is selectively rotatable relative to the element.

8. A surgical instrument as recited in claim 1, wherein at least one of the members includes an adaptor disposed between the member and the part, the adaptor including a moveable ramp interface such that the part is releasably engageable with the member.

9. A surgical instrument as recited in claim 8, wherein the adaptor includes a quick release connection including a push button release.

10. A surgical instrument as recited in claim 1, wherein the part of the second member includes an anterior blade positioned between the first blade and the second blade.

11. A surgical instrument as recited in claim 10, wherein the part of the third member includes a posterior blade positioned between the first blade and the second blade such that the posterior blade is spaced apart from the anterior blade.

12. A surgical instrument as recited in claim 1, wherein the element comprises a linear configuration.

13. A surgical instrument as recited in claim 1, wherein the element includes an arcuate configuration.

14. A surgical instrument as recited in claim 1, wherein the element includes a hub.

15. A surgical instrument as recited in claim 1, further comprising a dilator having a substantially oval shape and being engageable with tissue adjacent a spine.

16. A surgical instrument comprising:
an element connectable with a fixture;
a first arm independently and selectively movable relative to the element and including a housing having a cranial blade and a shaft slidably disposed in the housing, the shaft including a blade arm and a caudal blade that is coupled to the blade arm, the shaft defining a longitudinal axis, the caudal blade being coupled to the shaft such that the caudal blade is prevented from translating relative to the shaft along the longitudinal axis, the blade arm including a flange and a lever that is pivotable relative to the flange to facilitate rotation of the blade arm about an axis defined by the blade arm;
a second arm independently and selectively movable relative to the element and including an anterior blade; and
a third arm independently and selectively movable relative to the element and including a posterior blade,
wherein the arms are disposable in a configuration to space tissue of an incision to define an oblique surgical pathway relative to a bilateral axis of a body, the element comprising a collar having a radially splined surface that rotatably engages a radially splined surface of a collar of the fixture to simultaneously rotate the members relative to the fixture.

17. A surgical instrument as recited in claim 16, wherein the housing comprises a lock configured to engage teeth of the shaft to selectively space the caudal blade from the cranial blade.

18. A surgical instrument as recited in claim 16, wherein the cranial blade is coupled to the housing by the blade arm.

19. A surgical instrument as recited in claim 18, wherein the caudal blade is coupled to the shaft by a second blade arm, the second blade arm being rotatable relative to the shaft, the second blade arm including a second flange and a second lever that is pivotable relative to the second flange to facilitate rotation of the second blade arm about an axis defined by the second blade arm.

20. A surgical system comprising:
a dilator engageable with tissue of a body adjacent a spine; and
a surgical instrument including an element connectable with a fixture, a first arm independently movable relative to the element and including first and second blades engageable with tissue of a cranial-caudal portion of an incision relative to the body, a second arm independently movable relative to the element and including a blade engageable with tissue of an anterior portion of the incision, and a third arm independently movable relative to the element and including a blade engageable with tissue of a posterior portion of the incision, the first arm comprising a housing having the first blade and a shaft slidably disposed in the housing, the shaft including a first blade arm that is coupled to the second blade, the shaft defining a longitudinal axis, the second blade being coupled to the shaft by a second blade arm such that the second blade is prevented from translating relative to the shaft along the longitudinal axis, the first blade arm including a flange and a lever that is pivotable relative to the flange to facilitate rotation of the first blade arm about an axis defined by the first blade arm, the second blade arm including a flange and a lever that is pivotable relative to the flange to facilitate rotation of the second blade arm about an axis defined by the second blade arm,
wherein the arms are disposable in a configuration to space tissue of the incision to define an oblique surgical pathway relative to a bilateral axis of the body, the element comprising a collar having a radially splined surface that rotatably engages a radially splined surface of a collar of the fixture to simultaneously rotate the members relative to the fixture, the element comprising a knob that is connected to the collar of the element, the knob being configured to force the splined surfaces into engagement to lock the element with the fixture.

* * * * *